US007521588B2

(12) United States Patent
Stone et al.

(10) Patent No.: US 7,521,588 B2
(45) Date of Patent: *Apr. 21, 2009

(54) POLYMERIC WEB EXHIBITING A SOFT AND SILKY TACTILE IMPRESSION

(75) Inventors: Keith Joseph Stone, Fairfield, OH (US); Brian Francis Gray, Cincinnati, OH (US); Norman Scott Broyles, Hamilton, OH (US); Dimitris Ioannis Collias, Mason, OH (US); Yann-Per Lee, Vernon Hills, IL (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/127,472

(22) Filed: May 12, 2005

(65) Prior Publication Data
US 2005/0209575 A1 Sep. 22, 2005

Related U.S. Application Data

(63) Continuation of application No. 10/324,366, filed on Dec. 20, 2002, now Pat. No. 7,402,723.

(51) Int. Cl.
*A61F 13/15* (2006.01)
*B32B 3/10* (2006.01)
*B32B 5/14* (2006.01)
(52) U.S. Cl. ............... 604/378; 604/370; 604/380; 604/383; 428/131; 428/134; 428/136; 428/138; 428/170; 428/171

(58) Field of Classification Search ............... 604/378, 604/370, 380, 383; 428/131–140, 170–172
See application file for complete search history.

(56) References Cited

U.S. PATENT DOCUMENTS 3,949,127 A 4/1976 Ostermeier et al.

(Continued)

FOREIGN PATENT DOCUMENTS

EP 0 304 617 B1 1/1995

(Continued)

OTHER PUBLICATIONS

PCT International Search Report dated Apr. 5, 2004.

(Continued)

*Primary Examiner*—Jacqueline F. Stephens
(74) *Attorney, Agent, or Firm*—Gary J. Foose; Roddy M. Bullock

(57) ABSTRACT

A polymeric web exhibiting a soft and silky tactile impression on at least one side thereof is disclosed. The silky feeling side of the web exhibits a pattern of discrete hair-like fibrils, each of the hair-like fibrils being a protruded extension of the web surface and having a side wall defining an open proximal portion and a closed distal portion. The hair-like fibrils exhibit a maximum lateral cross-sectional diameter of between 2 and 5 mils, and an aspect ratio from 1 to 3. Methods and apparatus for making the polymeric web utilize a three-dimensional forming structure having a plurality of protrusions being generally columnar forms having an average aspect ratio of at least about 1.

43 Claims, 11 Drawing Sheets

U.S. PATENT DOCUMENTS

| | | | |
|---|---|---|---|
| 4,151,240 A | 4/1979 | Lucas | |
| 4,327,730 A | 5/1982 | Sorensen | |
| 4,342,314 A | 8/1982 | Radel | |
| 4,343,848 A | 8/1982 | Leonard, Jr. | |
| 4,456,570 A | 6/1984 | Thomas | |
| 4,463,045 A | 7/1984 | Ahr | |
| 4,514,345 A | 4/1985 | Johnson et al. | |
| 4,528,239 A | 7/1985 | Trokhan | |
| 4,591,523 A | 5/1986 | Thompson | |
| 4,601,868 A | 7/1986 | Radel | |
| 4,609,518 A * | 9/1986 | Curro et al. | 264/504 |
| 4,629,643 A | 12/1986 | Curro | |
| 4,634,440 A | 1/1987 | Widlund | |
| 4,690,679 A | 9/1987 | Mattingly, III | |
| 4,695,422 A | 9/1987 | Curro | |
| 4,741,941 A | 5/1988 | Englebert et al. | |
| 4,778,644 A | 10/1988 | Curro | |
| 4,806,303 A | 2/1989 | Bianco | |
| 4,839,216 A | 6/1989 | Curro | |
| 4,846,821 A | 7/1989 | Lyons | |
| 5,242,632 A | 9/1993 | Mende | |
| 5,269,981 A | 12/1993 | Jameson | |
| 5,520,875 A | 5/1996 | Wnuk | |
| 5,567,376 A | 10/1996 | Turi | |
| 5,585,017 A | 12/1996 | James | |
| 5,670,110 A | 9/1997 | Dirk | |
| 5,763,044 A | 6/1998 | Ahr et al. | |
| 5,822,833 A | 10/1998 | James | |
| 5,824,352 A | 10/1998 | Yang | |
| 5,827,597 A | 10/1998 | James | |
| 5,906,786 A | 5/1999 | James | |
| 5,914,184 A | 6/1999 | Morman | |
| 5,916,462 A | 6/1999 | James | |
| 5,997,986 A | 12/1999 | Turi | |
| 5,998,696 A | 12/1999 | Schone | |
| 6,022,607 A | 2/2000 | James | |
| 6,117,524 A | 9/2000 | Hisanaka | |
| H1927 H | 12/2000 | Chen et al. | |
| 6,228,462 B1 | 5/2001 | Lee | |
| 6,240,817 B1 | 6/2001 | James | |
| 6,300,258 B1 | 10/2001 | Stano | |
| 6,312,640 B1 | 11/2001 | Shimalla | |
| 6,417,426 B1 | 7/2002 | Takai | |
| 6,440,111 B1 * | 8/2002 | Berba et al. | 604/385.01 |
| 6,452,063 B1 | 9/2002 | Curro et al. | |
| 6,468,626 B1 | 10/2002 | Takai | |
| 6,479,130 B1 | 11/2002 | Takai | |
| 6,503,597 B2 | 1/2003 | Takai | |
| 6,503,598 B1 | 1/2003 | Goda | |
| 6,506,473 B1 | 1/2003 | Hisanaka | |
| 6,548,158 B2 | 4/2003 | Mizutani | |
| RE38,105 E | 5/2003 | James | |
| 6,852,475 B2 | 2/2005 | Stone et al. | |
| 2001/0014796 A1 | 8/2001 | Mizutani | |
| 2004/0118811 A1 | 6/2004 | Stone et al. | |
| 2004/0119207 A1 | 6/2004 | Stone et al. | |
| 2004/0119208 A1 | 6/2004 | Gray et al. | |
| 2004/0121120 A1 | 6/2004 | Gray et al. | |
| 2004/0247833 A1 | 12/2004 | Copat et al. | |
| 2005/0191496 A1 | 9/2005 | Gray et al. | |

FOREIGN PATENT DOCUMENTS

| | | |
|---|---|---|
| EP | 0 858 792 A2 | 8/1998 |
| EP | 0 862 904 A2 | 9/1998 |
| EP | 0 919 212 A2 | 6/1999 |
| EP | 1 062 927 A2 | 12/2000 |
| EP | 1 095 645 A2 | 5/2001 |
| EP | 1 110 526 A2 | 6/2001 |
| EP | 1 118 315 A2 | 7/2001 |
| EP | 1 121 916 A2 | 8/2001 |
| EP | 1 133 962 A1 | 9/2001 |
| EP | 1 138 299 A2 | 10/2001 |
| EP | 1 138 300 A2 | 10/2001 |
| EP | 1 283 019 A1 | 2/2003 |
| JP | 2741821 | 4/1998 |
| JP | 2 831 677 | 12/1998 |
| JP | 2849204 | 1/1999 |
| JP | 2001-105504 | 4/2001 |
| JP | 2001-129017 | 5/2001 |
| WO | WO 94/20054 | 9/1994 |
| WO | WO 97/00656 | 1/1997 |
| WO | WO 97/31601 A1 | 9/1997 |
| WO | WO 98/29071 A1 | 7/1998 |
| WO | WO 99/30658 A1 | 6/1999 |
| WO | WO 00/25714 | 5/2000 |
| WO | WO 00/59431 A1 | 10/2000 |
| WO | WO 01/03626 A1 | 1/2001 |
| WO | WO 01/43969 A1 | 6/2001 |
| WO | WO 02/098338 A1 | 12/2002 |

OTHER PUBLICATIONS

Notice of Allowance for U.S. Appl. No. 10/324,366; P&G Case 9135; dated Apr. 10, 2008.

Office Action for U.S. Appl. No. 10/324,366; P&G Case 9135; dated Jun. 26, 2007.

Office Action for U.S. Appl. No. 10/324,366; P&G Case 9135; dated Dec. 26, 2006.

Office Action for U.S. Appl. No. 10/324,366; P&G Case 9135; dated Apr. 21, 2006.

Office Action for U.S. Appl. No. 10/324,366; P&G Case 9135; dated Dec. 29, 2005.

Office Action for U.S. Appl. No. 10/324,366; P&G Case 9135; dated Aug. 25, 2005.

U.S. Appl. No. 11/893,426, filed Aug. 16, 2007, Gray et al.

Decision on Appeal Before the Board of Patent Appeals and Interferences, Ex parte Brian Francis Gray and Keith Joseph Stone, Appeal 2007-2198; U.S. Appl. No. 10/324,181, Technology Center 1700, Decided: Sep. 20, 2007.

Interview Summary for U.S. Appl. No. 10/388,779; P&G Case 9137RC; dated Nov. 19, 2008.

Office Action for U.S. Appl. No. 10/388,779; P&G Case 9137RC; dated Sep. 5, 2008.

U.S. Appl. No. 10/325,323, filed Dec. 20, 2002, Office Action dated Sep. 29, 2008.

U.S. Appl. No. 10/388,779, filed Mar. 14, 2003, Declaration Under 37 C.F.R. §1.132 by K. Stone.

* cited by examiner

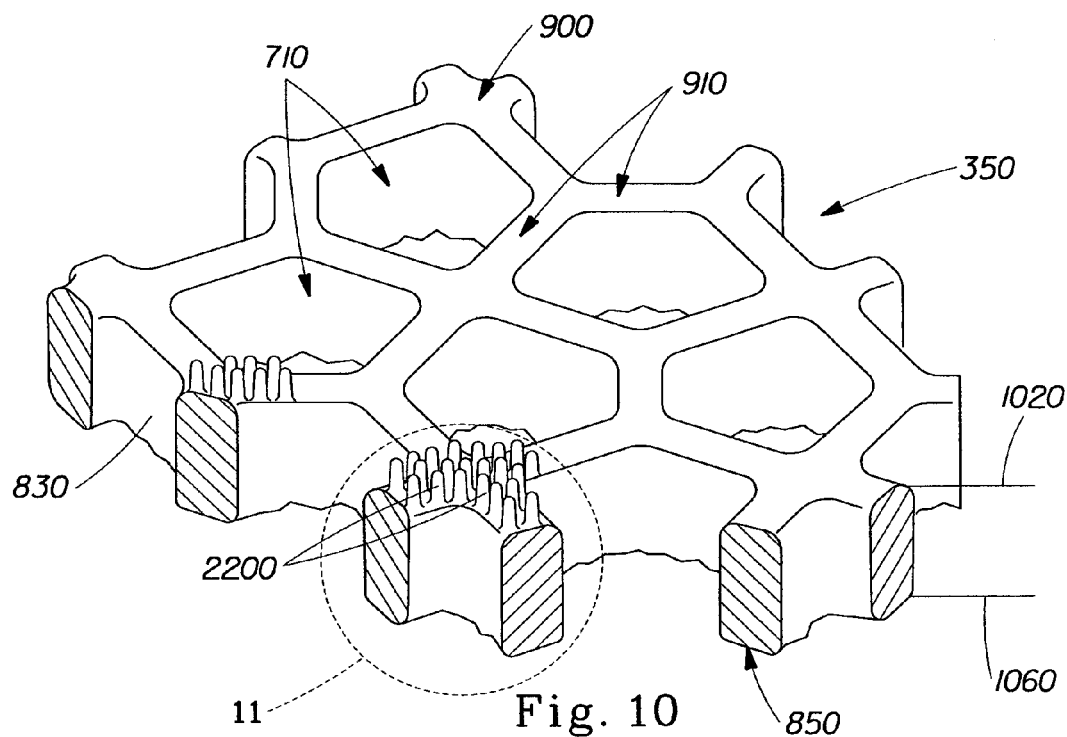
Fig. 10
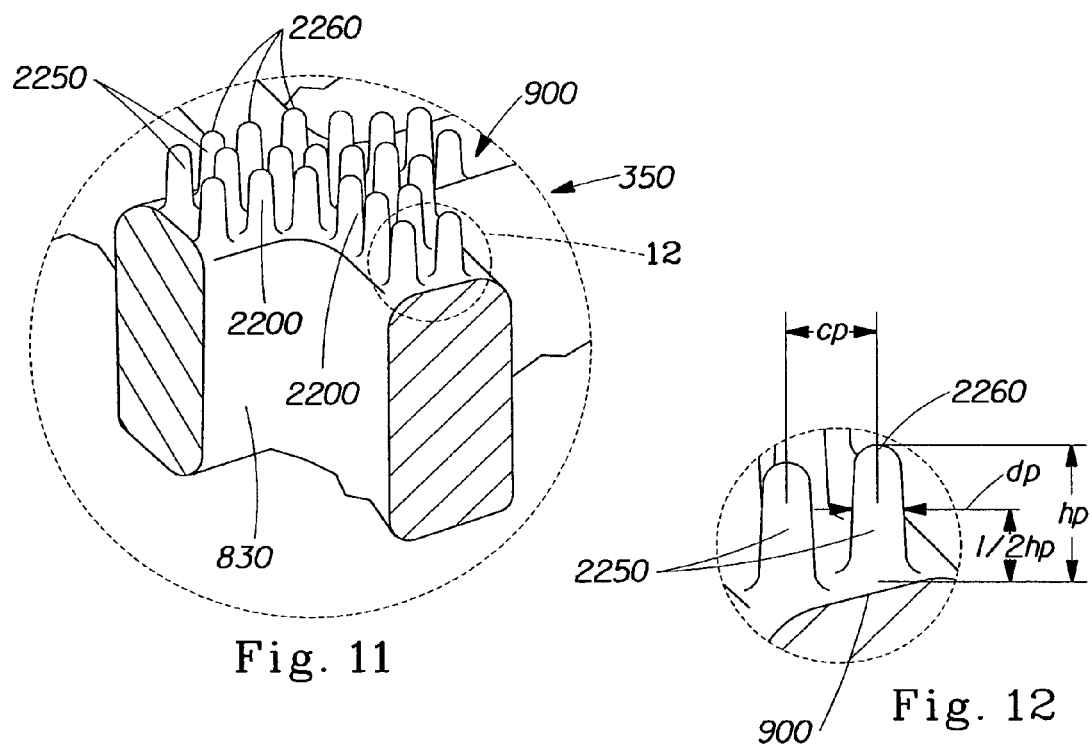
Fig. 11
Fig. 12

POLYMERIC WEB EXHIBITING A SOFT AND SILKY TACTILE IMPRESSION

CROSS REFERENCE TO RELATED APPLICATION

This application is a continuation of U.S. application Ser. No. 10/324,366, filed Dec. 20, 2002 now U.S. Pat. No. 7,402,723.

FIELD OF THE INVENTION

The present invention relates to a polymeric web exhibiting a soft and silky tactile impression on at least one surface. More particularly, the present invention relates a three-dimensional polymeric web exhibiting a soft and silky tactile impression that can be used as a body-facing topsheet in disposable absorbent.

BACKGROUND OF THE INVENTION

It is extremely desirable to construct disposable articles, such as absorptive devices, including sanitary napkins, pantyliners, interlabial devices, diapers, training pants, incontinent devices, wound dressings and the like, with a soft cloth-like surface feel to the user's skin at any anticipated points of contact. Likewise, it has long been known in the disposable articles art to construct absorptive devices that present a dry surface feel to the user, especially during use. By having a soft, cloth-like body-facing surface that retains a dry surface feel during use, an absorptive device gives improved wearing comfort, and minimizes the development of undesirable skin conditions due to prolonged exposure to moisture absorbed within the absorptive device.

While woven and non-woven fibrous webs are often employed as body-facing topsheets for absorptive devices because of their pleasant surface feel, macroscopically expanded, three dimensional, apertured polymeric webs such as the commercially successful DRI-WEAVE™ topsheet marketed by Procter & Gamble Company have also been utilized. One viable polymeric web of this type is disclosed in U.S. Pat. No. 4,342,314 issued to Radel et al. on Aug. 3, 1982. Such webs have been shown to exhibit desirable fluid transport and fluid retaining characteristics. Desirable fluid transport characteristics allow the topsheet to acquire fluids, such as urine or menses, and pass to fluid into the absorptive article. Once absorbed into the absorptive article, the fluid retaining feature of the topsheet preferably prevents rewet, i.e., the movement of fluid back through the topsheet. Rewet can be a result of at least two causes: (1) squeezing out of the absorbed fluid due to pressure on the absorptive article; and/or (2) wetness entrapped within or on the topsheet. Preferably, both properties, fluid acquisition and fluid retention, are maximized. Said differently, preferably a topsheet will exhibit high rates of fluid acquisition, and low levels of rewet.

Other macroscopically expanded, three dimensional, apertured polymeric webs are known. For example, U.S. Pat. No. 4,463,045 issued to Ahr et al. on Jul. 31, 1984 discloses a macroscopically expanded three-dimensional polymeric web that exhibits a substantially non-glossy visible surface and cloth-like tactile impression. Ahr et al. teaches the criteria which must be met with respect to the regularly spaced pattern of surface aberrations in order to diffusely reflect incident light and thereby eliminate gloss. Ahr, et al teaches that the surface aberrations in the web should exhibit an average amplitude of at least about 0.2 mils (i.e., 0.0002 inches), and most preferably at least about 0.3 mils (i.e., 0.0003 inches) for a more clothlike or fiberlike tactile impression in the resultant web. Despite its advancements in eliminating gloss, the structure of the surface aberrations of the web in Ahr, et al. can lack desired softness. As recognized in the art, for example is U.S. Pat. No. 4,629,643, issued to Curro et al. (discussed below), the lack of desired softness is believed to be due to the structure of each aberration, which can be described as having the properties of an "arch" that behaves as a discrete structural unit, resisting deflection. This lack of sufficient deflection detracts from the softness impression experienced by the user's skin.

One proposed solution to improve the softness impression to the web of Ahr et al., was disclosed in the aforementioned U.S. Pat. No. 4,629,643 (Curro, et al. '643) Curro, et al. '643 discloses a microapertured polymeric web exhibiting a fine scale pattern of discrete surface aberrations. Each of these surface aberrations have a maximum amplitude and, unlike the web structure disclosed in Ahr, et al. at least one microaperature is provided that is substantially coincidental with the maximum amplitude of each surface aberration. The forming of microapertures at the maximum amplitude of each surface aberration provides a volcano-like cusp with petal shaped edges. It is believed that the resultant web surface that is in contact with the human skin is of smaller total area and is less resistant to compressive and shear forces than the unapertured "arch-like" structures taught by Ahr et al.

Although the microapertured film of Curro, et al. '643 imparts superior tactile impression to the skin of the user, it has some drawbacks related to certain fluid handling properties when used as a topsheet in absorbent articles. For example, it has been found that a web as disclosed in Curro, et al. '643, when used as a topsheet on a sanitary pad can permit an unacceptably high amount of rewet, i.e., fluid that returns back to the skin-facing surface of the topsheet after initially having passed through the topsheet to be absorbed by the sanitary napkin. In particular, it appears that a web according to Curro '643 can be more susceptible to rewet under pressure. This is because when such a product is used as a topsheet in a catamenial product, for example, absorbed fluid can be urged back out of the product through the many microapertures of the topsheet. It appears that each of the microapertures in the structure of Curro, et al. '643 can provide a pathway for fluid to escape from an underlying absorbent core in an absorbent article under the pressure of normal wearing conditions. These pathways in the web structures therefore cause decreased fluid retention and increased rewet in the absorbent structures.

Attempts at alleviating the shortcoming of Curro '643, i.e., attempts to both maximize softness and reduce rewet, can be found, for example, in U.S. Pat. No. 6,228,462 issued to Lee, et al., on May 8, 2001. Lee discloses a compression resistant web comprising rigid polymers. The compression resistance of the rigid polymers helps reduce rewet, but the rigid polymers utilized tend to decrease the softness of the web.

Furthermore, the hydroforming processes disclosed in Curro, et al. '643 and Lee ''462 for making macroscopically expanded, three dimensional, apertured polymeric webs results in a formed film that must be dried after hydroforming. Due to the many interstices of the microapertures that can retain water, drying commercial quantities of these webs consumes significant amounts of energy, and can require significant capital investments in drying equipment. One example of an approach to effectively dry such webs is disclosed in U.S. Pat. No. 4,465,422 issued Sep. 22, 1987 to Curro, et al.

One further drawback associated with the webs disclosed in Curro '643 and Lee '462 when used as topsheets on sanitary napkins is the tendency of the microapertures to entrap fluid, such as menses. The entrapment can be in the microapertures themselves and/or between adjacent microapertures. Fluid so entrapped remains at or near the surface of the web, and can, therefore be in contact with the wearer's skin for prolonged periods of time. This contact negatively affects the skin health of the wearer and causes the topsheet to not have a clean appearance post-use.

Another attempt at making a soft, three-dimensional, macroscopically-expanded web having an improved functional surface is U.S. Pat. No. 5,670,110, issued to Dirk, et al. on Sep. 23, 1997. The web of Dirk et al. utilizes fibrils achieved via a screen printing roll. However, screen printing is a relatively slow process for making commercial webs for consumer articles.

Accordingly, it would be beneficial to have an improved formed film web that has superior tactile impression and superior fluid handling properties.

Additionally, it would be beneficial to have a formed film web that has superior tactile impression and provides for superior fluid retention and rewet characteristics.

Additionally, it would be beneficial to have a formed film web that has superior tactile impression and provides for superior cleanliness for hygiene articles.

Additionally, it would be beneficial to have an improved process for making a formed film web that has superior tactile impression and provides for superior fluid retention and rewet characteristics.

Finally, it would be beneficial to have an improved apparatus for use as a forming structure for forming a formed film web that has superior tactile impression and provides for superior fluid retention and rewet characteristics.

SUMMARY OF THE INVENTION

A polymeric web exhibiting a soft and silky tactile impression on at least one side thereof is disclosed. The silky feeling side of the web exhibits a pattern of discrete hair-like fibrils, each of the hair-like fibrils being a protruded extension of the web surface and having a sidewall defining an open proximal portion and a closed distal portion. The hair-like fibrils exhibit a maximum lateral cross-sectional diameter of between 2 and 5 mils, and an aspect ratio from 1 to 3.

BRIEF DESCRIPTION OF THE DRAWING

While the specification concludes with claims particularly pointing out and distinctly claiming the subject matter of the present invention, it is believed that the invention will be better understood from the following description taken in conjunction with the accompanying Figures, in which:

FIG. 10 is an enlarged, partially segmented, perspective illustration of a forming structure of the present invention.

FIG. 11 is a further enlarged, partial view of a portion of the forming structure shown in FIG. 10.

FIG. 12 is a further enlarged partial view of a portion of the forming structure shown in FIG. 11.

DETAILED DESCRIPTION OF THE INVENTION

Figure 1:
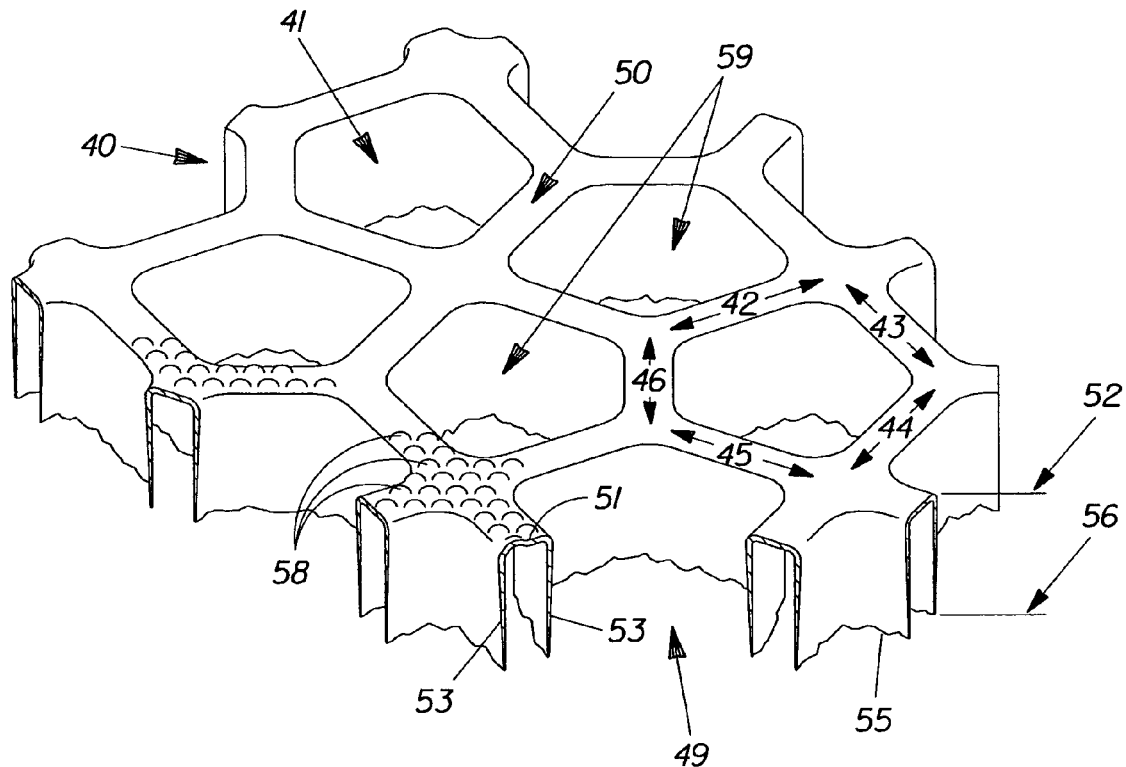
FIG. 1 is an enlarged, partially segmented, perspective illustration of a prior art polymeric web of the type generally disclosed in commonly assigned U.S. Pat. No. 4,342,314.

FIG. 1 is an enlarged, partially segmented perspective illustration of a prior art macroscopically-expanded, three-dimensional, fluid pervious polymeric web 40 formed generally in accordance with the aforementioned U.S. Pat. No. 4,342,314. Webs of this type have been found to be highly suitable for use as a topsheet in absorbent articles such as sanitary napkins, pantyliners, interlabial devices, and the like. The fluid pervious web 40 exhibits a plurality of macroscopic surface aberrations that can be apertures, such as primary apertures 41. Primary apertures 41 are formed by a multiplicity of interconnecting members, such as fiber like elements, e.g., 42, 43, 44, 45 and 46, that are interconnected to one another to define a continuous first surface 50 of the web 40. Each fiber like element has a base portion, e.g., base portion 51, located in plane 52 of first surface 50. Each base portion has a sidewall portion, e.g., sidewall portion 53, attached to each longitudinal edge thereof. The sidewall portions extend generally in the direction of a discontinuous second surface 55 of web 40. The intersecting sidewall portions are interconnected to one another intermediate the first and second surfaces of the web, and terminate substantially concurrently with one another in the plane 56 of the second surface 55. In some embodiments, the base portion 51 may have surface aberrations 58 in accordance with the aforementioned Ahr '045 patent.

As used herein, the term "macroscopically expanded" refers to the structure of a web formed from a precursor web or film, e.g., a planar web, that has been caused to conform to the surface of a three-dimensional forming structure so that both sides, or surfaces, of the precursor web are permanently altered due to at least partial conformance of the precursor web to the three-dimensional pattern of the forming structure. Such macroscopically-expanded webs are typically caused to conform to the surface of the forming structure by embossing (i.e., when the forming structure exhibits a pattern comprised primarily of male projections), by debossing (i.e., when the forming structure exhibits a pattern comprised primarily of female depressions, or apertures), or by a combination of both.

As used herein, the term "macroscopic" refers to structural features or elements that are readily visible and distinctly discernable to a human having 20/20 vision when the perpendicular distance between the viewer's eye and the web is about 12 inches. Conversely, the term "microscopic" is utilized to refer to structural features or elements that are not readily visible and distinctly discernable to a human having 20/20 vision when the perpendicular distance between the viewer's eye and the plane of the web is about 12 inches. In general, as used herein, the primary apertures of a web disclosed herein are macroscopic, and surface aberrations, such as hair-like fibrils as disclosed more fully below are considered microscopic.

The term "planar" as used herein to refers to the overall condition of a precursor web or film when viewed by the naked eye on a macroscopic scale, prior to permanently deforming the web into a three-dimensional formed film. In this context, extruded films prior to post-extrusion processing and films that do not exhibit significant degree of permanent macroscopic three-dimensionality, e.g., deformation out of the plane of the film, would generally be described as planar.

As utilized herein, the term "interconnecting members" refers to some or all of the elements of a web, e.g., web 40 in FIG. 1, portions of which serve to define the primary apertures by a continuous network. As can be appreciated from the description of FIG. 1 and the present invention herein, the interconnecting members, e.g., fiber like elements 42, 43, 44, 45, and 46, are inherently continuous, with contiguous interconnecting elements blending into one another in mutually adjoining transition portions. Individual interconnecting members can be best described with reference to FIG. 1 as those portions of the web disposed between any two adjacent primary apertures, originating in the first surface and extending into the second surface. On the first surface of the web the interconnecting members collectively form a continuous network, or pattern, the continuous network of interconnecting members defining the primary apertures, and on the second surface of the web interconnecting sidewalls of the interconnecting members collectively form a discontinuous pattern of secondary apertures. Interconnecting members are described more generally below with reference to FIG. 6.

In a three-dimensional, macroscopically-expanded web, the interconnecting members may be described as channel-like. Their two dimensional cross-section may also be described as "U-shaped", as in the aforementioned Radel '314 patent, or "upwardly concave-shaped", as disclosed in U.S. Pat. No. 5,514,105, issued on May 7, 1996 to Goodman, Jr., et al. "Upwardly-concave-shaped" as used herein, and as represented in FIG. 1, describes the orientation of the channel-like shape of the interconnecting members with relation to the surfaces of the web, with a base portion 51 generally in the first surface 50, and the legs, e.g., sidewall portions 53, of the channel extending from the base portion 51 in the direction of the second surface 55, with the channel opening being substantially in the second surface 55. In general, for a plane cutting through the web, e.g., web 40, orthogonal to the plane, e.g., plane 52, of the first surface 50 and intersecting any two adjacent primary apertures, e.g., apertures 41, the resulting cross-section of an interconnecting member disposed therein will exhibit a generally upwardly concave shape that may be substantially U-shaped.

The term "continuous" when used herein to describe the first surface of a macroscopically-expanded, three-dimensional formed film web, refers to the uninterrupted character of the first surface generally in the plane of the first surface. Thus, any point on the first surface can be reached from any other point on the first surface without substantially leaving the first surface. Conversely, as utilized herein, the term "discontinuous" when used to describe the second surface of a three-dimensionally formed film web refers to the interrupted character of the second surface generally in the plane of the second surface. Thus, any point on the second surface cannot necessarily be reached from any other point on the second surface without substantially leaving the second surface in the plane of the second surface.

Figure 2:
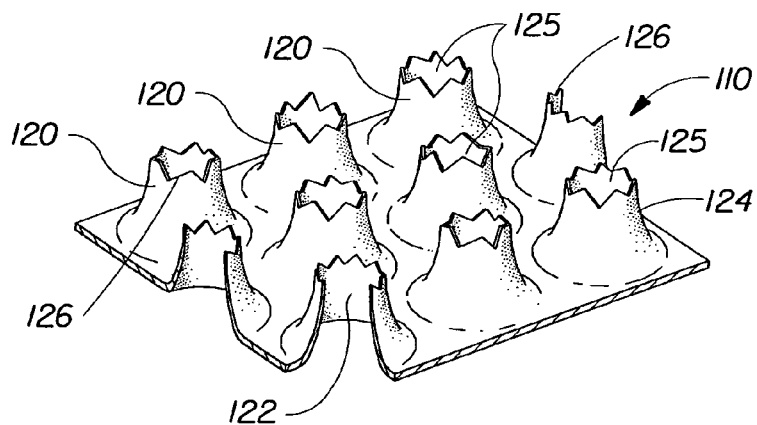
FIG. 2 is an enlarged, partially segmented, perspective illustration of a prior art polymeric web of the type generally disclosed in commonly assigned U.S. Pat. No. 4,629,643.

FIG. 2 shows an enlarged, partially segmented, perspective illustration of a portion of another prior art polymeric microapertured web 110 formed generally in accordance with the aforementioned Curro '643 patent. The microapertured surface aberrations 120 can be formed by a hydroforming process in which a high-pressure liquid jet is utilized to force the web to conform to a three-dimensional support member. As shown, ruptures which coincide substantially with the maximum amplitude of each micropertured surface aberration 120 result in the formation of a volcano-shaped aperture 125 having relatively thin, irregularly shaped petals 126 about its periphery. The relatively thin, petal-shaped edges of the aperture of such a web provide for increased softness impression on the skin of a user when compared, for example, to the web of Ahr '045. It is believed that this softness impression is due to the relative lack of resistance to compression and shear afforded by the surface aberrations having volcano-shaped apertures.

As mentioned above, although the microapertured film of Curro '643 imparts a superior tactile impression of softness, it can also permit undesirable rewet when used as a topsheet on a disposable absorbent article. The web of the present invention solves this problem by providing for softness via surface aberrations that exhibit low resistance to compression and shear, comparable to the web of Curro '643, and yet do not permit fluid flow via microapertures. Therefore, one benefit of the web of the present invention is superior softness together with minimal rewet when used as a topsheet on a disposable absorbent article, such as a sanitary napkin.

Figure 3:
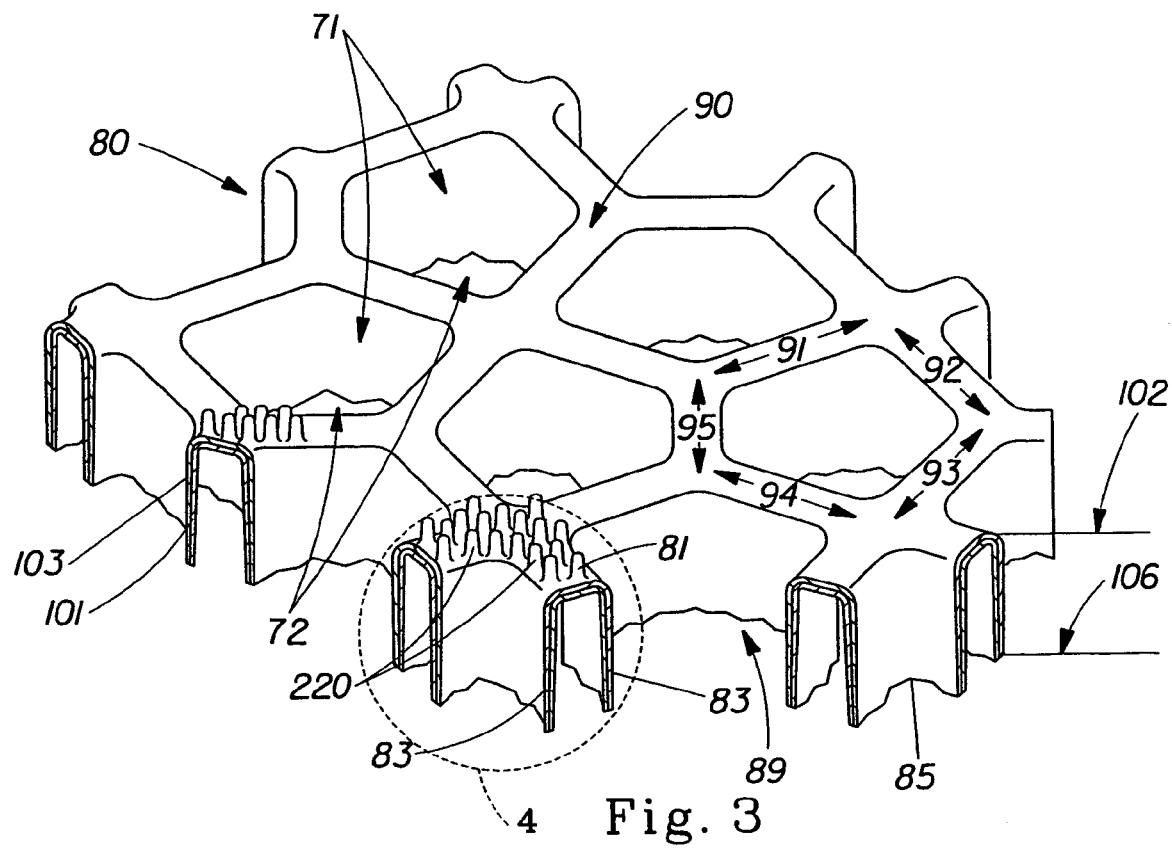
FIG. 3 is an enlarged, partially segmented, perspective illustration of a polymeric web of the present invention.

FIG. 3 is an enlarged, partially segmented perspective illustration of a fluid pervious, macroscopically-expanded, three-dimensional polymeric web 80 of the present invention. The geometric configuration of the macroscopic surface aberrations, e.g., primary apertures 71, of the polymeric web can be generally similar to that of the prior art web 40 illustrated in FIG. 1. Primary apertures 71 may be referred to as "apertures" or "macroapertures" herein, and refer to openings in the web that permit fluid communication between a first surface 90 of web 80 and a second surface 85 of web 80. The primary apertures 71 of the web shown in FIG. 3 are defined in the plane 102 of first surface 90 by a continuous network of interconnecting members, e.g., members 91, 92, 93, 94, and 95 interconnected to one another. The shape of primary apertures 71 as projected in the plane of the first surface 90 may be in the shape of polygons, e.g., squares, hexagons, etc., in an ordered or random pattern. In a preferred embodiment primary apertures 71 are in the shape of modified ovals, and in one embodiment primary apertures 71 are in the general shape of a tear drop. Polymer web 80 exhibits a plurality of surface aberrations 220 in the form of hair-like fibrils 225, described more fully below.

In a three-dimensional, microapertured polymeric web 80 of the present invention, each interconnecting member comprises a base portion, e.g., base portion 81, located generally in plane 102, and each base portion has sidewall portions, e.g., sidewall portions 83 extending from each longitudinal edge thereof. Sidewall portions 83 extend generally in the direction of the second surface 85 of the web 80 and join to sidewalls of adjoining interconnecting members intermediate the first and second surfaces, 90 and 85, respectively, and terminate substantially concurrently with one another to define secondary apertures, e.g., secondary apertures 72 in the plane 106 of second surface 85.

Figure 6:
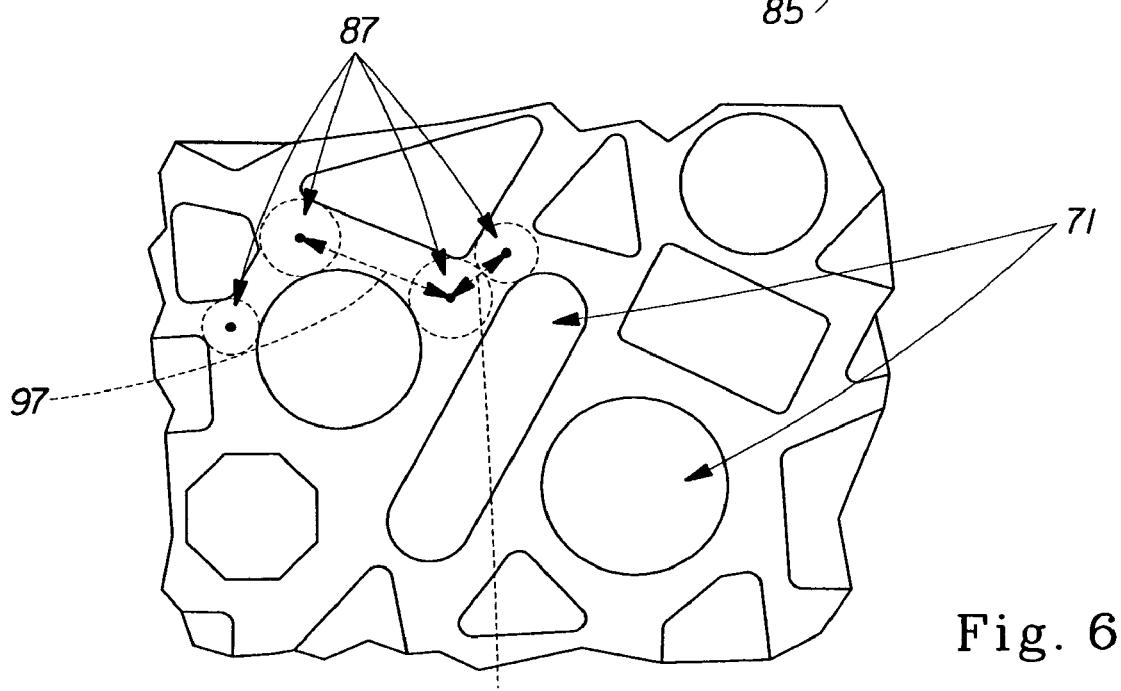
FIG. 6 is a plan view of representative aperture shapes projected in the plane of the first surface of a polymeric web of the present invention.

FIG. 6 is a plan view of representative primary aperture shapes projected in the plane of the first surface of an alternative embodiment of a three-dimensional, macroapertured polymer web of the present invention. While a repeating pattern of uniform shapes, for example a tessellating pattern, is preferred, the shape of primary apertures, e.g., apertures 71, may be generally circular, polygonal, or mixed, and may be arrayed in an ordered pattern or in a random pattern.

As shown in FIG. 6 the interconnecting members, e.g., interconnecting members 97 and 98, are each inherently continuous, with contiguous interconnecting elements blending into one another in mutually adjoining transition zones or portions, e.g., portions 87. In general transition portions are defined by the largest circle that can be inscribed tangent to any three adjacent apertures. It is understood that for certain patterns of apertures the inscribed circle of the transition portions may be tangent to more than three adjacent apertures. For illustrative purposes, interconnecting members may be thought of as beginning or ending substantially at the centers of the transition portions, such as interconnecting members 97 and 98. Interconnecting members need not be linear, but may be curvilinear. The sidewalls of the interconnecting members can be described as interconnecting to the sidewalls of adjacent, contiguous interconnecting members. Exclusive of portions of the transition zones and portions including hair-like fibrils, as disclosed below, cross-sections of interconnecting members transverse to the longitudinal centerline between the beginning and end of the interconnecting member may be generally described as U-shape. However, the transverse cross-section need not be uniform or U-shaped along the entire length of the interconnecting member, and for certain primary aperture configurations it may not be uniform along most of its length. In particular, in transition zones or portions interconnecting members blend into contiguous interconnecting members and transverse cross-sections in the transition zones or portions may exhibit substantially non-uniform U-shapes, or no discernible U-shape.

Figure 4:
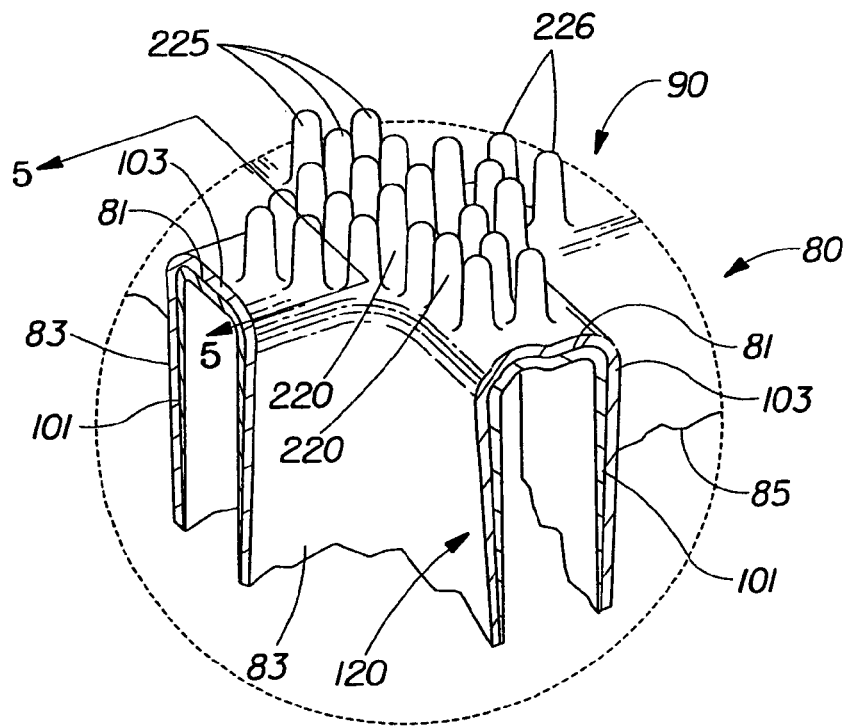
FIG. 4 is a further enlarged, partial view of a portion of the web shown in FIG. 3 illustrating in greater detail certain features of the polymeric web of the present invention.

FIG. 4 is a further enlarged, partial view of the three-dimensional polymeric web 80 shown in FIG. 3. The three-dimensional polymeric web 80 comprises a polymer film 120, i.e., the precursor film, which can be a single layer of extruded polymer or a multilayer coextruded or laminate film. As shown in FIG. 4, film 120 is a two layer laminate comprising a first layer 101 and a second layer 103. Laminate materials may be coextruded, as is known in the art for making laminate films, including films comprising skin layers. While it is presently preferred that, as shown in FIG. 4, the polymeric layers, e.g., layers 101 and 103, terminate substantially concurrently in the plane of the second surface 106 it is not presently believed to be essential that they do so. One or more layers may extend further toward the second surface than the other(s).

FIG. 4 shows a plurality of surface aberrations 220 in the form of hair-like fibrils 225. The hair-like fibrils are formed as protruded extensions of the polymeric web 80, generally on the first surface 90 thereof. The number, size, and distribution of hair-like fibrils 225 on polymeric web 80 can be predetermined based on desired skin feel. For applications as a topsheet in disposable absorbent articles, it is preferred that hair-like fibrils 225 protrude only from the base portion 81 in first surface 90 of polymeric web 80, as shown in FIGS. 3 and 4. Therefore, when web 80 is used as a topsheet in a disposable absorbent article, the web can be oriented such that the hair-like fibrils 225 are skin contacting for superior softness impression, and yet, the hair-like fibrils 225 do not obstruct fluid flow through macroapertures 71. Moreover, having hair-like fibrils 225 with closed distal portions 226 results in reduced rewet, i.e., reduced amounts of fluid being re-introduced to the surface of the topsheet after having been first passed through the topsheet to underlying absorbent layers.

Figure 5:
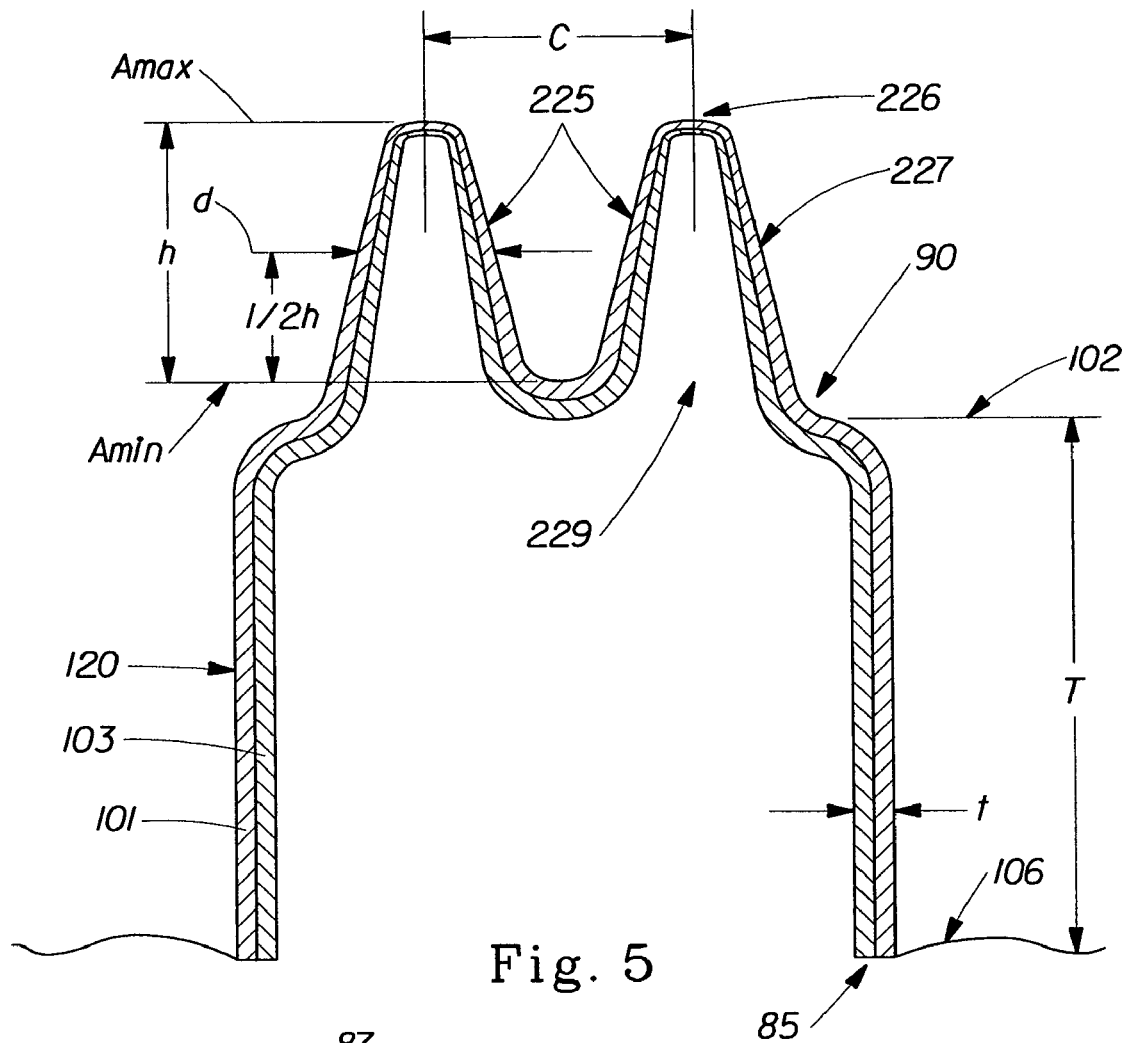
FIG. 5 is a cross-sectional depiction of a cross section taken along Section 5-5 of FIG. 4.

As shown in cross-section FIG. 5, hair-like fibrils 225 can be described as protruding from first surface 90 of web 80. As such, hair-like fibrils 225 can be described as being integral with film 120, and formed by permanent local plastic deformation of film 120. Hair-like fibrils can be described as having a sidewall 227 defining an open proximal portion 229 and a closed distal portion 226. Hair-like fibrils 225 have a height h measured from a minimum amplitude $A_{min}$ between adjacent fibrils to a maximum amplitude $A_{max}$ at the closed distal portion 226. Hair-like fibrils have a diameter d, which for a generally cylindrical structure is the outside diameter at a lateral cross-section. By "lateral" is meant generally parallel to the plane of the first surface 102. For non-uniform lateral cross-sections, and/or non-cylindrical structures of hair-like fibrils, diameter d is measured as the average lateral cross-sectional dimension at ½ the height h of the fibril, as shown in FIG. 5. Thus, for each hair-like fibril 225, an aspect ratio, defined as h/d, can be determined. Hair-like fibrils 225 can have an aspect ratio h/d of at least 0.5. The aspect ratio can be 1, or 1.5 and is preferably at least about 2.

In general, because the actual height h of any individual hair-like fibril 225 can be difficult to determine, and because the actual height may vary, an average height $h_{avg}$ of a plurality of hair-like fibrils can be determined by determining an average minimum amplitude $A_{min}$ and an average maximum amplitude $A_{max}$ over a predetermined area of web 80. Likewise, for varying cross-sectional dimensions, an average dimension $d_{avg}$ can be determined for a plurality of hair-like fibrils 225. Such amplitude and other dimensional measurements can be made by any method known in the art, such as by computer aided scanning microscopy and data processing. Therefore, an average aspect ratio $AR_{avg}$ of the hair-like fibrils 225 for a predetermined portion of the web can be expressed as $h_{avg}/d_{avg}$.

The dimensions h and d for hair-like fibrils 225 can be indirectly determined based on the known dimensions of a forming structure, as disclosed more fully below. For example, for a forming structure made according to predetermined dimensions of male protrusions, e.g., protrusions 2250 shown in FIG. 11 below, on which hair-like fibrils 225 are to be formed can have known dimensions. If precursor film 120 is fully and permanently deformed over protrusions 2250, then h and d can be calculated from these known dimensions, taking into account the thickness of the precursor film 120, including predicted and/or observed web thinning. If the precursor film 120 is not fully formed over protrusions 2250, then the height h of hair-like pillars will be less than the corresponding height of the protrusions 2250.

In one embodiment the diameter of hair-like fibrils 225 is constant or decreases with increasing amplitude (amplitude increases to a maximum at closed distal end 226). As shown in FIG. 5, for example, the diameter, or average lateral cross-sectional dimension, of hair-like fibrils 225 can be a maximum at proximal portion 229 and the lateral cross-sectional dimension steadily decreases to distal end 226. This structure is believed to be necessary to ensure the polymeric web 80 can be readily removed from the forming structure 350, as more fully described below with respect to FIG. 10.

As shown in FIG. 5, some thinning of precursor web 120 can occur due to the relatively deep drawing required to form high aspect ratio hair-like fibrils 225. For example, thinning can be observed at or near closed distal ends 226. By "observed" is meant that the thinning is distinct when viewed in magnified cross-section. Such thinning can be beneficial as the thinned portions offer little resistance to compression or shear when touched by a person's skin. For example, when a person touches the polymeric web 80 on the side exhibiting hair-like fibrils 225, the finger tips first contact closed distal ends 226 of hair-like fibrils 225. Due to the high aspect ratio of hair-like fibrils 225, and, it is believed, to the wall thinning of the film at or near the distal ends 226, the hair-like fibrils offer little resistance to the compression or shear imposed on the web by the person's fingers. This lack of resistance is registered as a feeling of softness, much like the feeling of a velour fabric. In fact, it has been found that polymeric webs of the present invention can provide for a feeling of softness equal to or greater than that of prior art polymeric webs, such as the web disclosed in Curro '643.

It should be noted that a fluid impermeable web having only the hair-like fibrils as disclosed herein, and not having macroscopic apertures, can offer softness for any application in which fluid permeability is not required. Thus, in one embodiment of the present invention, the invention can be described as a polymeric web 80 exhibiting a soft and silky tactile impression on at least one surface thereof, the silky feeling surface of the web 80 exhibiting a pattern of discrete hair-like fibrils 225, each of the hair-like fibrils 225 being a protruded extension of the web surface and having a side wall 227 defining an open proximal portion 229 and a closed distal portion 226, the hair-like fibrils maximum lateral cross-sectional dimension at or near said open proximal portion, exhibiting a cross-sectional diameter d of between about 50 microns (about 0.002 inch) to about 76 microns (about 0.003 inch), and can be at least 100 microns (0.004 inches) 130 microns (0.005 inches). The hair-like fibrils can have an aspect ratio from 0.5 to 3.

For disposable absorbent articles, where a topsheet having a fluid permeable, three-dimensional structure is desired, the invention can be described as a polymeric web 80 exhibiting a soft and silky tactile impression on at least one surface 90 thereof, the silky feeling surface 90 of the web exhibiting a pattern of discrete hair-like fibrils 225, each of the hair-like fibrils 225 being a protruded extension of the web surface 90 and having a side wall 227 defining an open proximal portion 229 and a closed distal portion 226, the hair-like fibrils exhibiting an average cross-sectional diameter d of between 50 microns (0.002 inches) 130 microns (0.005 inches), and an aspect ratio from at least 0.5, 1, 1.5, 2, or 3 and wherein the web 80 further exhibits a macroscopically expanded, three-dimensional pattern of macroscopic surface aberrations, e.g., primary apertures 71 superposed thereon, the macroscopic surface aberrations 71 being oppositely oriented from the hair-like fibrils 225, that is, the primary apertures extend from a first surface 90 to a second surface 85 of polymeric web 80.

The "area density" of the hair-like fibrils 225, which is the number of hair-like fibrils 225 per unit area of first surface 90, can be optimized for use in absorbent articles. In general, the center-to-center spacing can be optimized for adequate tactile impression, while at the same time minimizing fiber-to-fiber entrapment of fluid. Currently, it is believed that a center-to-center spacing of about 100 microns to 250 microns (about 0.004 inch to about 0.010 inch) is optimal for use in sanitary napkins. Minimizing entrapment of menses between fibers improves the surface cleanliness of the sanitary napkin, which, in turn improves the cleanliness and skin health of the wearer.

In one embodiment, "superposed thereon" means that the polymeric web appears generally as shown in FIG. 3, wherein the pattern of discrete hair-like fibrils 225 is disposed on the land areas 81 of the interconnecting members only, i.e., only on the first surface 90 of web 80. However, conceptually, it is contemplated that "superposed thereon" could also cover an embodiment (not shown) in which the pattern of discrete hair-like fibrils 225 extends into macroapertures 71, for example on side walls 83 of the interconnecting members. In other embodiments, hair-like fibrils 225 are disposed only in certain predetermined regions of web 80. For example, a topsheet for a sanitary napkin can have a central region having hair-like fibrils 225, and the remainder of the topsheet being free from hair-like fibrils 225.

Precursor web 120 can be any polymeric film having sufficient material properties to be formed into the web of the present invention by the hydroforming process described herein. That is, precursor web 120 must have sufficient yield properties such that the precursor web 120 can be strained without rupture to an extent to produce hair-like fibrils 225 and, in the case of a three-dimensional, macroscopically-apertured, formed film, rupture to form macroapertures 71. As disclosed more fully below, process conditions such as temperature can be varied for a given polymer to permit it to stretch with or without rupture to form the web of the present invention. In general, therefore, it has been found that preferred starting materials to be used as the precursor web 120 for producing the web 80 of the present invention exhibit a low yield and high-elongation characteristics. In addition, the starting films preferably strain harden. Examples of films suitable for use as the precursor web 120 in the present invention include films of low density polyethylene (LDPE), linear low-density polyethylene (LLDPE), and blends of linear low-density polyethylene and low density polyethylene (LDPE/LLDPE).

Precursor web 120 must also be sufficiently deformable and have sufficient ductility for use as a polymeric web of the present invention. The term "deformable" as used herein describes a material which, when stretched beyond its elastic limit, will substantially retain its newly formed conformation.

One material found suitable for use as a precursor web 120 of the present invention is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882).

Precursor web 120 can be a laminate of two or more webs, and can be a co-extruded laminate. For example, precursor web 120 can comprise two layers as shown in FIG. 4, and precursor web 120 can comprise three layers, wherein the inner most layer is referred to as a core layer, and the two outermost layers are referred to as skin layers. In one embodiment precursor web 120 comprises a three layer coextruded laminate having an overall thickness of about 25 microns (0.001 in.), with the core layer having a thickness of about 18 microns (0.0007 in.); and each skin layer having a thickness of about 3.5 microns (0.00015 in.). In general, for use as a topsheet in sanitary napkins, precursor web 120 should have an overall thickness (sometimes referred to as caliper) of at least about 10 microns and less than about 100 microns. The thickness of precursor web 120 can be about 15 microns, 20 microns, 25 microns, 30 microns, 35 microns, 40 microns, 45 microns, or 60 microns. In general, the ability to form high area density (or low average center-to-center spacing C) hair-like fibrils 225 on web 80 is limited by the thickness of precursor web 120. For example, it is believed that the center-to-center spacing C of two adjacent hair-like fibrils 225 should be greater than twice the thickness of precursor web 120 to permit adequate and complete three-dimensional web formation between adjacent protrusions 2250 of forming structure 350 as disclosed more fully below.

The precursor web 120 preferably comprises a surfactant. In a three layer laminate, the core layer can comprise a surfactant while the outer layers are initially devoid of surfactants. Preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, etyhoxylated anhydrosorbitol esters, ethoxylated natural fats, oils, and waxes, glycol esters of fatty acids, carboxylic amides, diethanolamine condensates, and polyalkyleneoxide block copolymers. Molecular weights of surfactants selected for the present invention may range from about 200 grams per mole to about 10,000 grams per mole. Preferred surfactants have a molecular weight from about 300 to about 1,000 grams per mole.

The surfactant level initially blended into precursor web 120 (or optionally the core layer in a three layer laminate) can be as much as 10 percent by weight of the total multilayer structure. Surfactants in the preferred molecular weight range (300-1,000 grams/mole) can be added at lower levels, generally at or below about 5 weight percent of the total multilayer structure.

The precursor web 120 can also comprise titanium dioxide in the polymer blend. Titanium dioxide can provide for greater opacity of the finished web 80. Titanium dioxide can be added at up to about 10 percent by weight to low density polyethylene for blending into the precursor web 120 material.

Other additives, such as particulate material, e.g., calcium carbonate ($CaCO_3$), particulate skin treatments or protectants, or odor-absorbing actives, e.g., zeolites, can be added in one or more layers of precursor web 120. In some embodiments, webs 80 comprising particulate matter, when used in skin-contacting applications, can permit actives to contact the skin in a very direct and efficient manner. Specifically, in some embodiments, formation of hair-like fibrils 225 can expose particulate matter at or near the distal ends thereof. Therefore, actives such as skin care agents can be localized at or near distal ends 226 to permit direct skin contact with such skin care agents when the web 80 is used in skin contacting applications.

The precursor web 120 can be processed using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a pre-compounding extruder followed by repelletization prior to film extrusion. Suitable methods for making precursor web 120 are disclosed in U.S. Pat. No. 5,520,875, issued to Wnuk et al. on May 28, 1996 and U.S. Pat. No. 6,228,462, issued to Lee et al. on May 8, 2001; both patents the disclosure of which is incorporated herein by reference.

A fluid pervious polymeric web of the present invention can be utilized as a topsheet on a catamenial device, such as a sanitary napkin. For example, a polymeric web 80 of the present invention exhibiting a macroscopically expanded, three-dimensional pattern of macroscopic surface aberrations in the form of primary apertures 71 combines softness properties with excellent fluid rewet properties (i.e., reduced fluid rewet compared to previous webs, such as the web of Curro '643).

Figure 7:
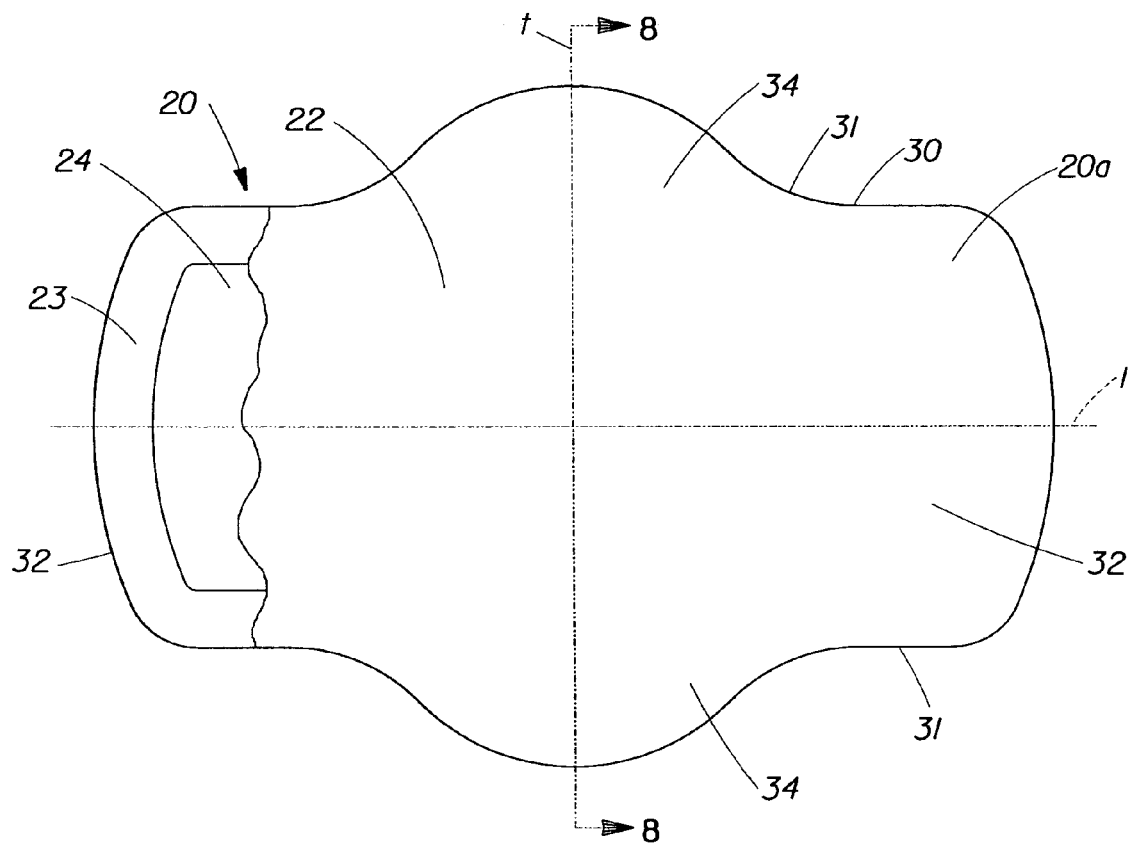
FIG. 7 is a top plan view of a sanitary napkin with portions cut away to more clearly show the construction of a catamenial device of the present invention.

FIG. 7 is a top plan view of a sanitary napkin 20 with portions cut away to more clearly show the construction of the napkin 20, including topsheet 22, which can comprise a polymeric web 80 of the present invention. It should be understood that the polymeric web 80 of the present invention can also be utilized in other absorbent articles such as pantyliners, interlabial devices, diapers, training pants, incontinent devices, wound dressings and the like. It also should be understood, that the present invention is not limited to the particular type or configuration of the sanitary napkin 20 shown in FIG. 7, which is simply a representative non-limiting example.

Figure 8:
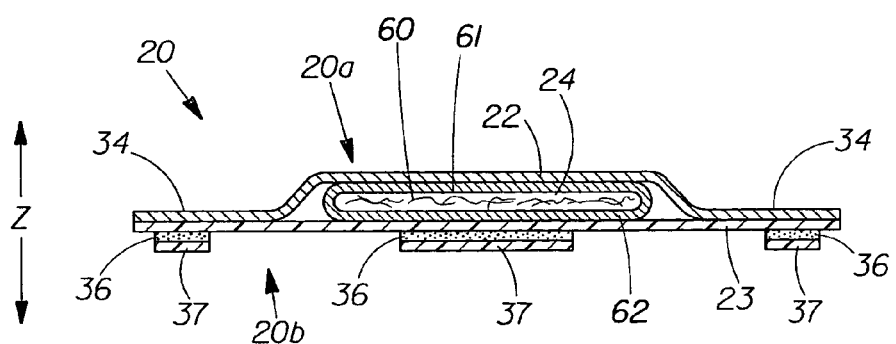
FIG. 8 is a cross-sectional view of the sanitary napkin taken along Section 8-8 of FIG. 7.

As shown in FIG. 8, the sanitary napkin 20 has two surfaces, a body-facing surface 20a and an opposed garment-facing surface 20b. The body-facing surface 20a is intended to be worn adjacent to the body of the wearer. The garment-facing surface 20b is intended to be placed adjacent to the wearer's undergarments when the sanitary napkin 20 is worn.

The sanitary napkin 20 has two centerlines, a longitudinal centerline "I" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

As shown in FIG. 7, the sanitary napkin 20 comprises a liquid pervious topsheet 22, which can comprise web 80 of the present invention, a liquid impervious backsheet 23 joined with the liquid pervious topsheet 22, and an absorbent core 24 positioned between the liquid pervious topsheet 22 and the liquid impervious backsheet 23. FIG. 7 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes optional sideflaps or "wings" 34 that can be folded around the crotch portion of the wearer's panties. The side flaps 34 can serve a number of purposes, including, but not limited to protecting the wearer's panties from soiling and keeping the sanitary napkin secured to the wearer's panties.

FIG. 8 is a cross-sectional view of the sanitary napkin taken along section line 8--8 of FIG. 7. As can be seen in FIG. 8, the sanitary napkin 20 preferably includes adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use. In addition to having a longitudinal direction and a transverse direction, the sanitary napkin 20 also has a "z" direction or axis, which is the direction proceeding down through the liquid pervious topsheet 22 and into whatever fluid storage core 24 that may be provided. A continuous path between the liquid pervious topsheet 22 and underlying layer or layers of the articles herein permits fluid to be drawn in the "z" direction and away from the topsheet of the article into its ultimate storage layer. In some embodiments, the continuous path will have a gradient of increasing capillary attraction, which facilitates fluid flow down into the storage medium.

Figure 9:
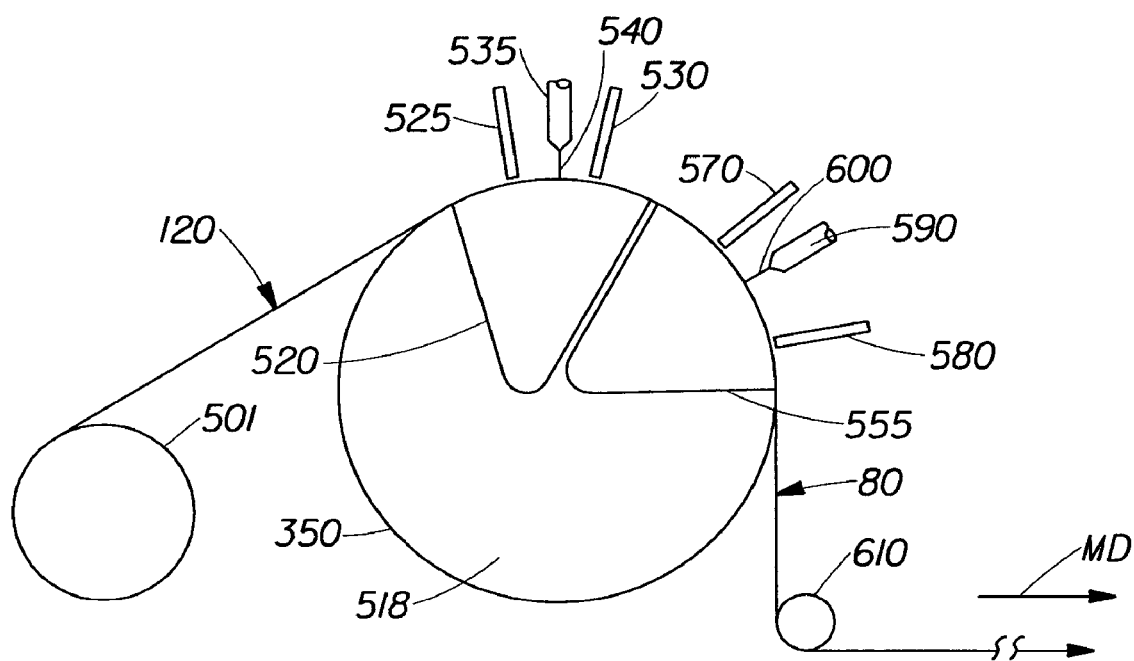
FIG. 9 is a simplified schematic illustration of a single phase forming process of the present invention.

In FIG. 9 there is shown single-phase web process for debossing and drying a continuous polymeric web 80 of the present invention. By single-phase is meant that the process uses only one three-dimensional forming structure. By continuous is meant to distinguish the described process from a batch process in which individual, discrete samples of web are made, often referred to as hand sheets. While it is recognized that webs of the present invention can be batch-processed using the structures described for the continuous process, a continuous process is the preferred method for commercially making a polymeric web of the present invention. Further, while the process described with respect to FIG. 9 is primarily designed to form macroscopically-expanded webs having hair-like fibrils 225 and primary apertures, e.g., apertures 71 of web 80, it is believed that a hydroforming process can be utilized to form a web having only hair-like fibrils by suitably modifying the forming structure to have only protrusions 2250.

Polymeric web 80 of the present invention can be formed by a hydroforming process on a single three-dimensional forming structure 350 and can also be annealed and/or dried on the forming structure 350 prior to rewinding the web into roll stock for further processing. The three-dimensional structures of a polymeric web, e.g., polymeric web 80 shown in FIG. 4, are formed by forcing the web to conform to the forming structure 350, which rotates about stationary forming drum 518. Forming structure 350 is described more fully below, but, in general, it is a three-dimensional form to which the precursor web 120 is forced to conform.

Precursor web 120 can be extruded and chilled immediately prior to being fed directly onto the surface of forming structure 350, or it can be fed from a supply roll, as shown by supply roll 501 in FIG. 9. In some embodiments it is preferred that the temperature of the precursor web 120 be elevated sufficiently to soften it and make it more conformable to the forming structure 350. The temperature of precursor web 120 can be elevated by applying hot air or steam to the web or by passing the web through heated nip rolls, prior to subjecting it to the forming process.

In the process described in FIG. 9, precursor web 120 is fed in a substantially planar condition in the machine direction (MD) from a supply roll 501 onto the surface of forming structure 350. Forming structure 350 rotates at a speed such that the tangential surface velocity of the forming structure 350 substantially matches that of the linear velocity of precursor web 120 in the machine direction, so that during the hydroforming process the web is substantially stationary relative to forming structure 350.

Once precursor web 120 is adjacent to and being "carried on", so to speak, the forming structure 350, precursor web 120 is directed over stationary vacuum chamber 520 which is interior to forming drum 518. Although the hydroforming process described herein can be accomplished to some degree without vacuum chambers, in general, vacuum chambers aid in better three-dimensional web formation as well as liquid removal. As precursor web 120 passes over vacuum chamber 520, the outwardly-exposed surface of precursor web 120 is impinged upon by a liquid jet 540 discharged from high pressure liquid jet nozzle 535 between a pair of stationary liquid baffles 525 and 530 which served to help localize splashing liquid. The effect of the liquid jet 540 is to cause the precursor web to conform to forming structure 350. As precursor web conforms to forming structure 350, both the hair-like fibrils 225 and the primary apertures 71 can be formed. As primary apertures 71 form, vacuum from vacuum chamber 520 aids in removing excess liquid from the web, and, in some cases aids in forming precursor web 120 to forming structure 350. As precursor web 120 is passed under the influence of high pressure liquid jet 540, it is permanently deformed to conform to the forming structure 350, thereby being formed into three-dimensional, macroscopically-expanded polymeric web 80 of the present invention.

In the process described with reference to FIG. 9, a single liquid jet 540 is described as forming both the hair-like fibrils 225 and the primary apertures 71. In another embodiment, additional liquid (or fluid) jets can be used to form the three-dimensional web structures in multiple stages. For example, a first fluid, such as water, can impinge precursor web 120 to form macroapertures 71 in a first stage, and following the first stage, a second fluid, such as hot water or air (optionally in combination with a vacuum chamber) can impinge the partially-formed web to form the hair-like fibrils 225 in a second stage.

In general, therefore, more than one fluid (e.g., water, air) can be directed to impinge on, and do energetic work on, precursor web 120 in stages. It is believed that, for thermoplastic precursor webs 120, as the temperature of the precursor web approaches its melting point, it more easily stretches without rupture to form over protrusions 2250 of forming structure 350. However, for forming macroapertures it is more desirable to have relatively high strain rates and relatively rapid rupture, and for forming hair-like fibrils it is more desirable to have relatively low strain rates and no rupture. Accordingly, in a two-stage forming process, the temperature of the impinging fluid at first and/or second stages can be adjusted independently, depending on the dwell time over which each impingement acts and the temperature of the precursor web 120 to form both macroapertures 71 and high aspect ratio hair-like fibrils 225 independently.

For making webs suitable for use as a topsheet in a disposable absorbent article, precursor web 120 can be a polyolefinic film from about 10 microns to about 100 microns in total thickness. For such precursor webs 120, high pressure liquid jet 540 is typically water at a temperature from about 15-95 degrees C., operated at a pressure in the range of about 200 psig to about 1200 psig and a water flow rate in the range of about 18 liters (4 gallons) per minute to about 62 liters (14 gallons) per minute per 25.4 cross-machine direction (CD) mm (1 inch) of width of the precursor web 120.

After passing beyond the high pressure liquid jet 540, (or jets, as discussed above), polymeric web 80 of the present invention can be dried while still on forming structure 350. For example, as shown in FIG. 9, polymeric web 80 can be directed, while still on forming structure 350, under the influence of drying means 590. Drying means 590 can be any of means for removing, or driving off liquids from polymeric webs, such as radiant heat drying, convective drying, ultrasonic drying, high velocity air knife drying, and the like. In general, a drying medium 600 can be utilized, such as heated air, ultrasonic waves, and the like. A stationary vacuum chamber 555 can be utilized to aid in drying by means of a partial pressure inside forming drum 518. Drying means 590 can be designed to drive liquid off of polymeric web 80 and into vacuum chamber 555. Baffles 570 and 580 can be utilized to locally contain any liquid that gets removed and does not enter vacuum chamber 555. Baffles 570 and 580 can also serve to localize and direct heat or heated air used for drying.

Using a heated drying medium 600 has an additional benefit for making webs 80 of the present invention. Prior art macroscopically-expanded, three-dimensional polymeric webs, such as the webs disclosed in Curro '643, are dried in a separate process after being removed form their respective forming structures. These webs are typically wound onto a roll for storage until needed for web processing of disposable articles, for example. One problem associated with prior art webs is the compression setting that occurs during winding and storage. Without being bound by theory, it is believed that three-dimensional polyethylene webs can experience a secondary crystallization over time which "locks in" the collapsed, wound state of the web. It has been found that by first annealing three-dimensional polymeric webs by subjecting them to elevated temperatures for a sufficient time, this observed compression set is reduced or prevented altogether. In general, however, it is difficult to subject prior art webs to the requisite temperatures due to the relatively fragile structure. That is, if a prior art web is subjected to annealing temperatures, the web tends to lose the three-dimensional structure formed on the forming structure. For this reason, therefore, drying the web while still on the forming structure provides a significant processing benefit by permitting processing with sufficiently high annealing temperatures to anneal the web, while at the same time drying it. The annealing temperature will vary depending on the time of drying, the polymer used and the thickness of the web, but, in general, for polyolefinic webs, a drying/annealing temperature of between about 50-250 degrees C. is sufficient.

After polymeric web 80 passes the drying (or drying/annealing) stage of the process it can be removed from the forming structure 350 about roller 610 and is thereafter rewound or fed directly to subsequent converting operations.

A forming structure of the present invention, such as forming structure 350 referred to with respect to FIG. 9, is necessary for making a web of the present invention. The forming structure is sometimes referred to as a forming screen. FIG. 10 shows a portion of a forming structure of the present invention 350 in partial perspective view. The forming structure 350 exhibits a plurality of forming structure apertures 710 defined by forming structure interconnecting members 910. Forming structure apertures 710 permit fluid communication between opposing surfaces, that is, between forming structure first surface 900 in the plane of the first surface 1020 and forming structure second surface 850 in the plane of the second surface 1060. Forming structure sidewall portions 830 extend generally between the forming structure first surface 900 and forming structure second surface 850. Protrusions 2200 extend from forming structure first surface 900 to form generally columnar, pillar-like forms.

A comparison of FIG. 10 with FIG. 3 shows the general correspondence of forming structure 350 with polymeric web 80 of the present invention. That is, the three-dimensional protrusions 2250 and depressions (e.g., apertures 710) of forming structure 350 have a one-to-one correspondence to the hair-like fibrils 225 and primary apertures 71, respectively, of polymeric web 80. The one-to-one correspondence is necessary to the extent that the forming structure 350 determines the overall dimensions of the polymeric web 80 of the present invention. However, the distance between plane of the first surface 102 and plane of the second surface 106 of the polymeric web 80 need not be the same as the distance between the plane of the first surface 1020 and the plane of the second surface 1060 of forming structure 350. This is because the distance "T" for polymeric web 80, as shown in FIG. 5, is not dependent upon the actual thickness of forming structure 350, the thickness being the perpendicular distance between the plane of the first surface 1020 and the plane of the second surface 1060 of forming structure 350.

FIG. 11 is a further enlarged, partial perspective view of the forming structure 350 shown in FIG. 10, and compares with the similar view of polymeric web 80 in FIG. 4. Protrusions 2250 can be made by methods described below to extend from first surface 900 to a distal end 2260. As shown in the further enlarged view of FIG. 12, protrusions 2250 can have a height hp measured from a minimum amplitude measured from first surface 900 between adjacent protrusions to distal end 2260. Protrusion height hp can be at least about 50 microns (about 0.002 inch) and can be at least about 76 microns (about 0.003 inch), and can be at least about 152 microns (about 0.006 inch), and can be at least about 250 microns (about 0.010 inch), and can be at least about 381 microns (about 0.015 inch). Protrusions 2250 have a diameter dp, which for a generally cylindrical structure is the outside diameter. For non-uniform cross-sections, and/or non-cylindrical structures of protrusions 2250, diameter dp is measured as the average cross-sectional dimension of protrusions at ½ the height hp of the protrusions 2250, as shown in FIG. 12. Protrusion diameter dp can be about 50 microns (about 0.002 inch), and can be at least about 76 microns (about 0.003 inch), and can be at least about 127 microns (about 0.005 inch). Thus, for each protrusion 2250, a protrusion aspect ratio, defined as hp/dp, can be determined. Protrusions 2250 can have an aspect ratio hp/dp of at least 1, and as high as 3 or more. The aspect ratio can be at least about 5 and can be about 6. The protrusions 2250 can have a center-to-center spacing Cp between two adjacent protrusions 2250 of between about 100 microns (about 0.004 inch) to about 250 microns (about 0.010 inch). In general, it is believed that the actual distance between two adjacent protrusions 2250 (i.e., a "side-to-side" dimension) should be greater than twice the thickness t of precursor web 120 to ensure adequate deformation of precursor web 120 between adjacent protrusions 2250.

In general, because the actual height hp of each individual protrusion 2250 may vary, an average height $hp_{avg}$ of a plurality of protrusions 2250 can be determined by determining a protrusion average minimum amplitude $Ap_{min}$ and a protrusion average maximum amplitude $Ap_{max}$ over a predetermined area of forming structure 350. Likewise, for varying cross-sectional dimensions, an average protrusion diameter $dp_{avg}$ can be determined for a plurality of protrusions 2250. Such amplitude and other dimensional measurements can be made by any method known in the art, such as by computer aided scanning microscopy and related data processing. Therefore, an average aspect ratio of the protrusions 2250, $ARp_{avg}$ for a predetermined portion of the forming structure 350 can be expressed as $hp_{avg}/dp_{avg}$. The dimensions hp and dp for protrusions 2250 can be indirectly determined based on the known specifications for making forming structure 350, as disclosed more fully below.

In one embodiment the diameter of protrusions 2250 is constant or decreases with increasing amplitude. As shown in FIG. 12, for example, the diameter, or largest lateral cross-sectional dimension, of protrusions 2250 is a maximum near first surface 900 and steadily decreases to distal end 2260. This structure is believed to be necessary to ensure that the polymeric web 80 can be readily removed from the forming structure 350.

Forming structure 350 can be made of any material that can be formed to have protrusions 2250 having the necessary dimensions to make a web of the present invention, is dimensionally stable over process temperature ranges experienced by forming structure 350, has a tensile modulus of at least about 5 MPa, a yield strength of at least about 5 MPa, and a strain at break of at least about 1%, preferably at least about 5%. Dimensional stability is necessary only for commercial processes as described with respect to FIG. 9, because for some process conditions the forming structure 350/forming drum 518 interface can be compromised if the forming structure 350 expands or contracts more than the forming drum 518. For batch processing of polymeric webs of the present invention dimensional stability is not a requirement. Process temperature ranges are affected by process conditions including the temperature of the fluid jet, e.g., liquid jet 540, and the temperature of forming structure 350, which can be heated, for example. In general, for polyolefinic webs, including laminated, co-extruded films for use in webs for disposable absorbent articles (i.e., films having a thickness, t, of about 10-100 microns), a water temperature of between 15 degrees C. and 95 degrees C. can be used. The drying/annealing air temperature can be 250 degrees C. or less. In general, process temperatures can be varied throughout a wide range and still make the polymeric web 80 of the present invention. However, the temperature ranges can be varied to make polymeric web 80 at optimal rates depending on film thickness, film type, and line speed.

In a preferred embodiment, protrusions 2250 are made integrally with forming structure 350. That is, the forming structure is made as an integrated structure, either by removing material or by building up material. For example, forming structure 350 having the required relatively small scale protrusions 2250 can be made by local selective removal of material, such as by chemical etching, mechanical etching, or by ablating by use of high-energy sources such as electrical-discharge machines (EDM) or lasers.

Figure 13:
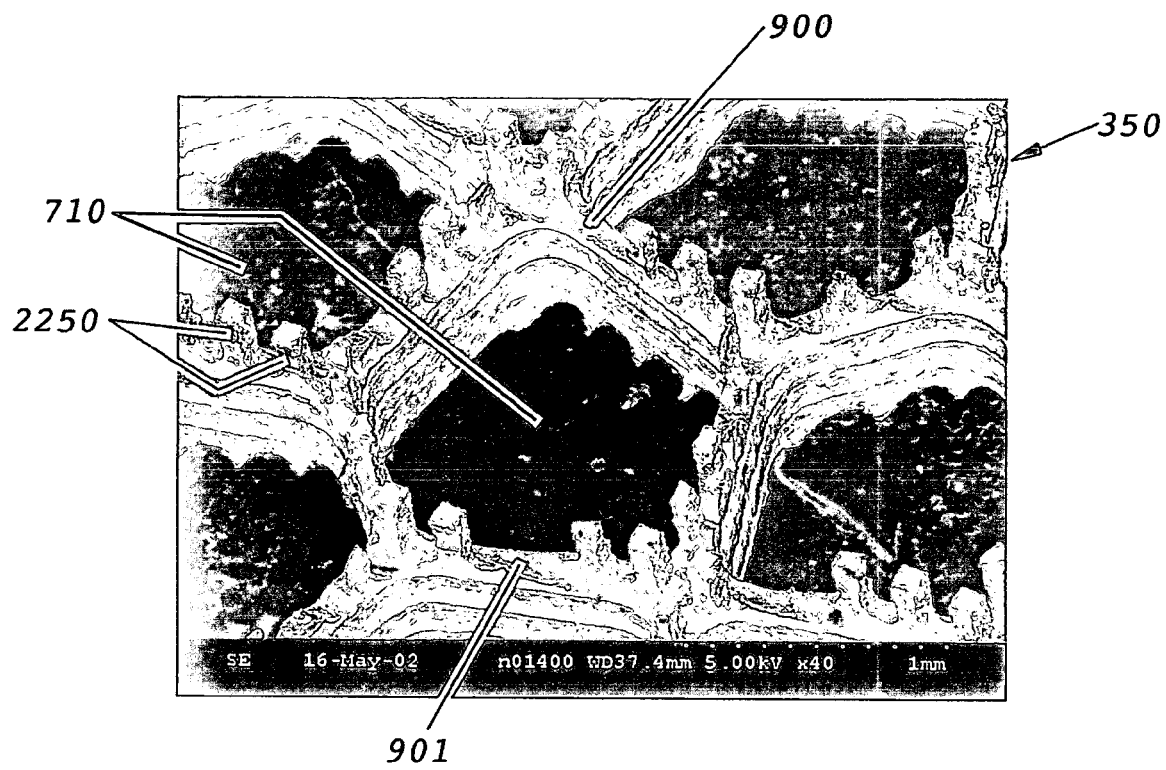
FIG. 13 is a photomicrograph of one embodiment of a forming structure of the present invention.
Figure 14:
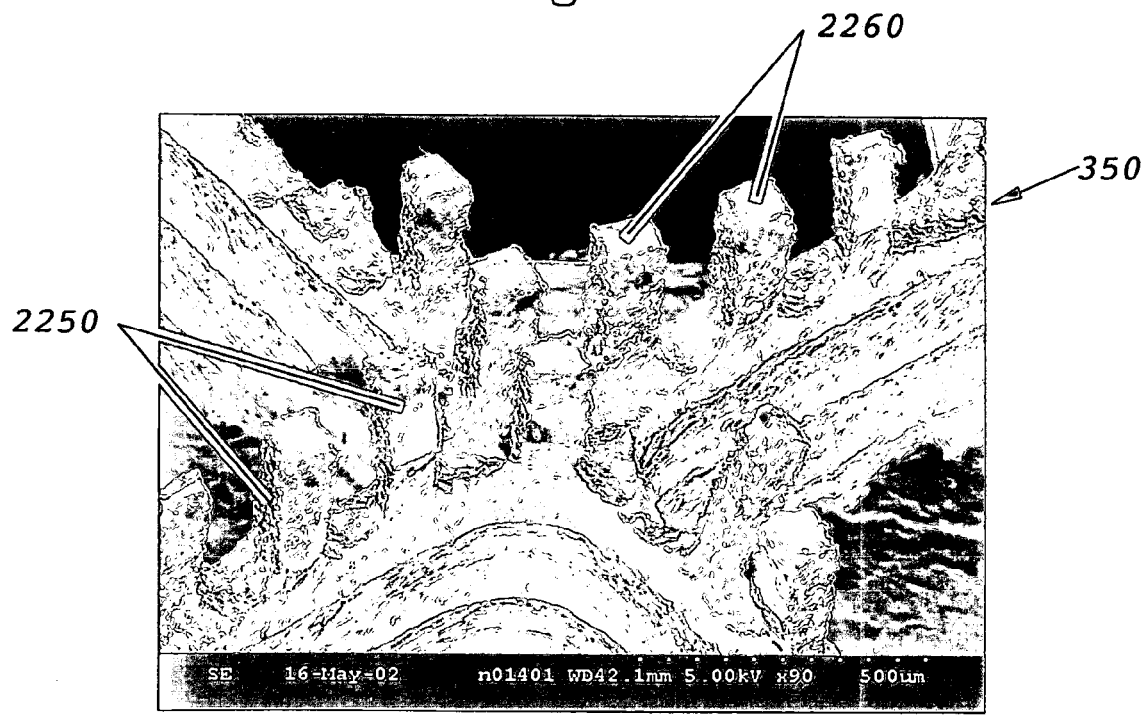
FIG. 14 is an enlarged view of a portion of the forming structure of FIG. 13.

A portion of a prototype forming structure 350 made of steel and having protrusions 2250 made by a conventional EDM process is shown in FIGS. 13 and 14. FIG. 13 is a photomicrograph of a forming structure 350 and FIG. 14 is a further enlarged view the forming structure of FIG. 13. As shown in FIG. 13, a steel forming structure has been subjected to an EDM process to form integral protrusions 2250 having distal ends 2260. The forming structure 350 shown in FIGS. 13 and 14 has depressions 710 generally similarly shaped to those shown in FIG. 3. However, as can be seen in FIGS. 13 and 14, the structure is less than ideal for making topsheets for absorbent articles because of the geometrical constraints of both the forming structure 350 prior to the EDM process, and the EDM process itself. Specifically, as can be seen, first surface 900 of forming structure interconnecting members 910 is only one protrusion "wide". Also, as can be seen in FIG. 13, due to the geometrical constraints of the process of EDM, gaps between protrusions 2250 can result. For example, gap 901 in FIG. 13 resulted from the EDM wire being oriented slightly off parallel from the respective forming structure interconnecting members 910 shown. Therefore, for commercially successful production of webs suitable for topsheets in disposable absorbent articles, the forming structure shown in FIG. 13 may not be acceptable. However, it is clear that suitably shaped protrusions 2250 having the required aspect ratios can be formed. The protrusions 2250 of the forming structure shown in FIG. 13 have an average height $hp_{avg}$ of about 275 microns (0.011 inch), and an average diameter of about $dp_{avg}$ of about 100 microns (0.004 inch), defining an average aspect ratio of $ARp_{avg}$ of about 2.7. (Note that the forming screen shown in FIGS. 13 and 14 is a prototype, and has been processed by EDM on both sides. In practice, it is only necessary to form protrusions on one side.)

In another method of making forming structure 350, a base material susceptible to laser modification is laser "etched" to selectively remove material to form protrusions 2250 and forming structure apertures 710. By "susceptible to laser modification" means that the material can be selectively removed by laser light in a controlled manner, recognizing that the wavelength of light used in the laser process, as well as the power level, may need to be matched to the material (or vice-versa) for optimum results. Currently known materials susceptible to laser modification include thermoplastics such as polypropylene, acetal resins, thermosets such as crosslinked polyesters, or epoxies, or even metals such as aluminum or stainless steel. Optionally, thermoplastic and thermoset materials can be filled with particulate or fiber fillers to increase compatibility with lasers of certain wavelengths of light and/or to improve modulus or toughness to make more durable protrusions 2250.

Figure 15:
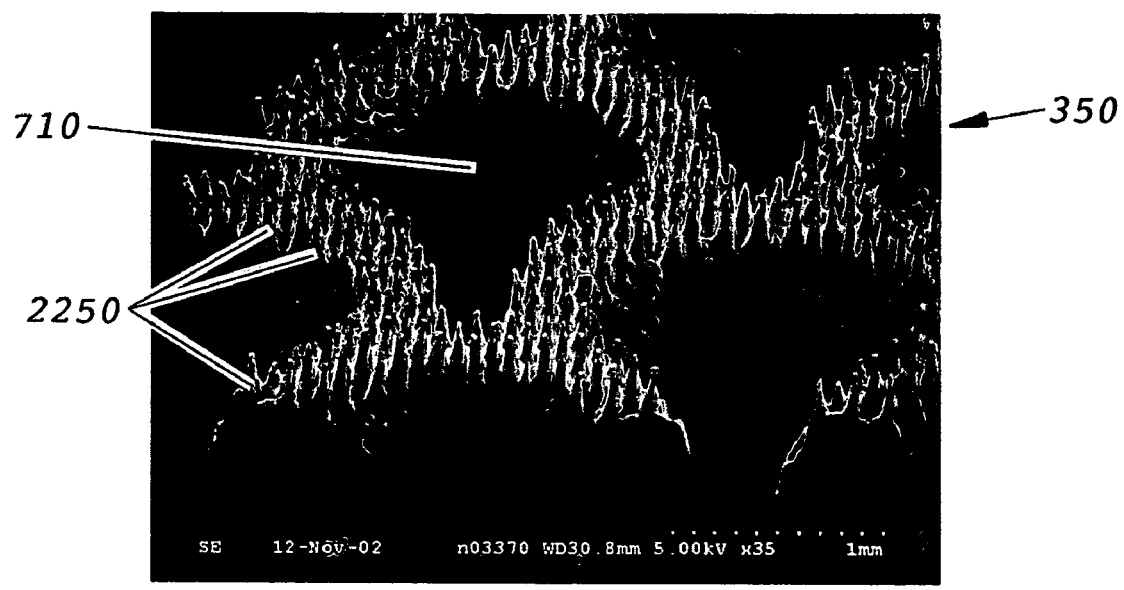
FIG. 15 is a photomicrograph of another embodiment of a forming structure of the present invention.
Figure 16:
FIG. 16 is an enlarged view of a portion of a forming structure similar to that shown in FIG. 15.

FIG. 15 is a photomicrograph of laser-etched embodiment of a forming structure 350 of the present invention. FIG. 16 is an enlarged view of another, but similar, forming structure 350 of the present invention. The forming structures 350 shown in FIGS. 15 and 16 are made by first forming a polymer layer having formed therein depressions 710, which as shown are generally "teardrop" shaped and would make generally teardrop shaped primary apertures 71 in web 80 of the present invention. The polymer layer having depressions 710 therein can be formed by radiating a liquid photosensitive resin such as a UV-light-curable polymer, through an appropriate masking layer on an underlying support layer (not shown) such as a foraminous woven backing. Suitable polymer layers, support layers, masking layers and UV-curing processes are well known in the art of making paper-making belts and are disclosed in U.S. Pat. No. 5,334,289 issued to Trokhan et al., on Aug. 2, 1994; and U.S. Pat. No. 4,529,480 issued to Trokhan on Jul. 16, 1985; and U.S. Pat. No. 6,010,598 issued to Boutilier et al. on Jan. 4, 2000, each of these patents, being hereby incorporated herein by reference for the teaching of structures, resins and curing techniques. As disclosed in the Boutilier '598 patent, for example, one suitable liquid photosensitive resin composition is comprised of four components: a prepolymer; monomers; photoinitiator and antioxidants. A preferred liquid photosensitive resin is Merigraph L-055 available from MacDermid Imaging Technology, Inc. of Wilmington, Del.

After the polymer layer is cured to have depressions 701 the polymer layer is laser etched to form protrusions 2250 having distal ends 2260. Laser etching can be achieved by known laser techniques, selecting wavelength, power, and time parameters as necessary to produce the desired protrusion dimensions. In the forming structure of FIG. 16, protrusions have an average height hp of 250 microns and an average diameter dp of 85 microns (at ½ height hp) and an aspect ratio arp of about 2.9.

In one embodiment, forming structure 350 formed as a cured polymer on a support layer can be used as is, with the support layer being a part of forming structure 350. However, in another embodiment, the cured polymer can be removed from the support layer and used alone. In this case, it may be desirable to only partially cure the polymer, remove the support layer 903 and finish fully curing the polymer material.

Figure 17:
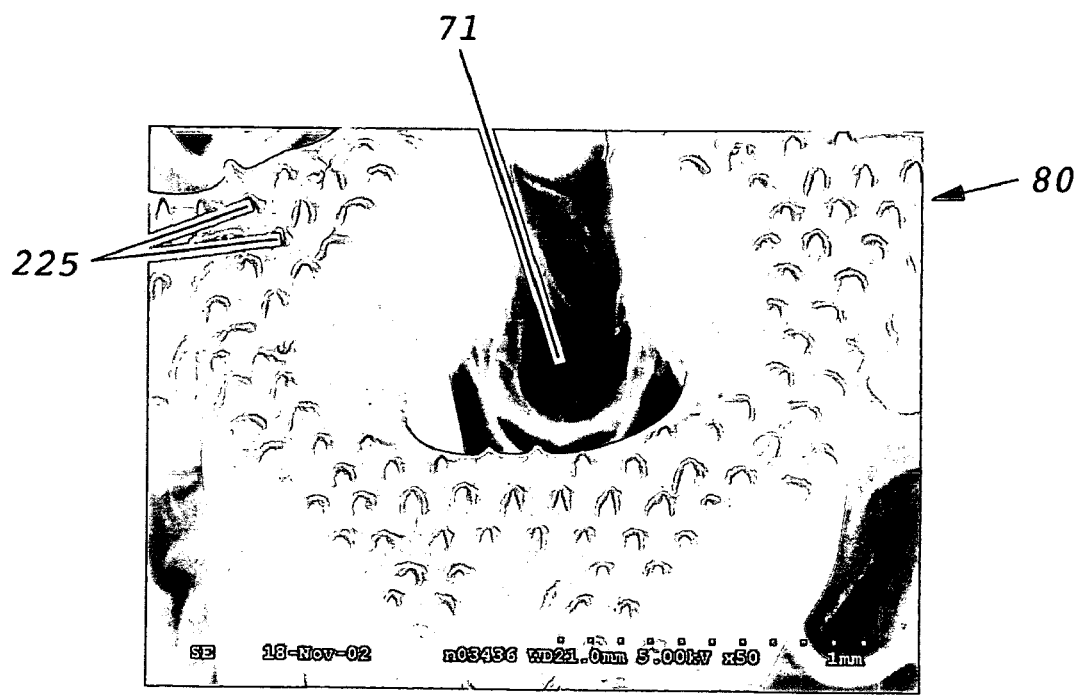
FIG. 17 is a photomicrograph of a portion of a web of the present invention.
Figure 18:
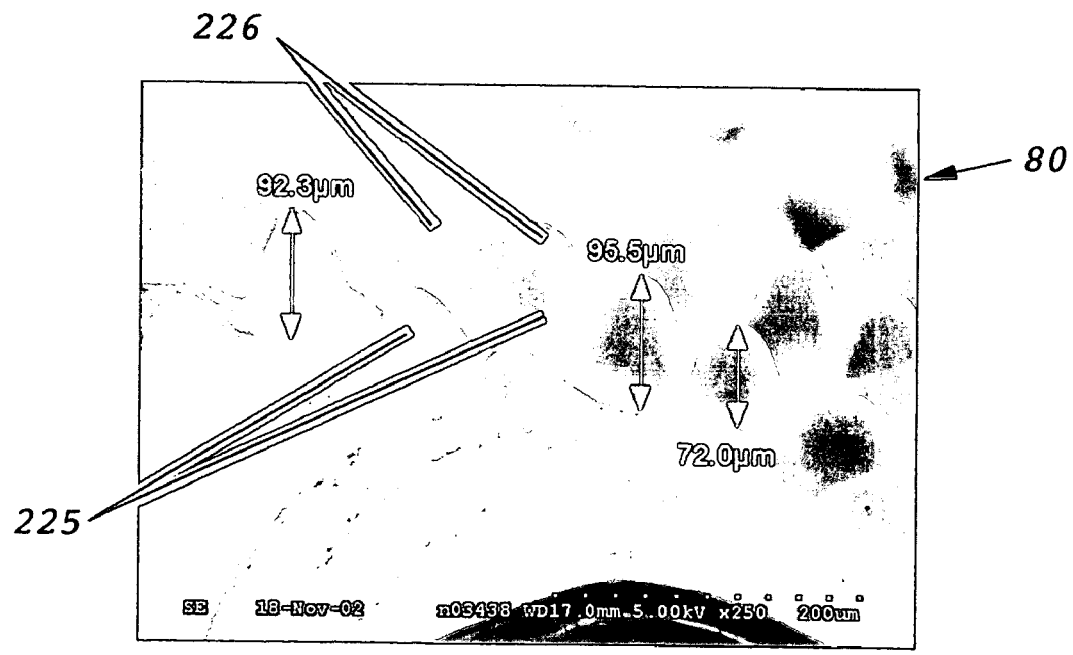
FIG. 18 is an enlarged view of a portion of the web shown in FIG. 17.

A web 80 made on the forming structure shown in FIG. 15 is shown in the photomicrographs of FIGS. 17 and 18. FIG. 17 is a photomicrograph of a portion of web 80 showing hair-like fibrils 225 and aperture 71. FIG. 18 is a further enlarged view of web 80 showing in more detail hair-like fibrils 225 having closed distal ends 226. The precursor web 120 for the web 80 shown in FIGS. 17 and 18 was made from a 25 micron (0.001 inch) thick Dowlex 2045A precursor film 120.

Figure 19:
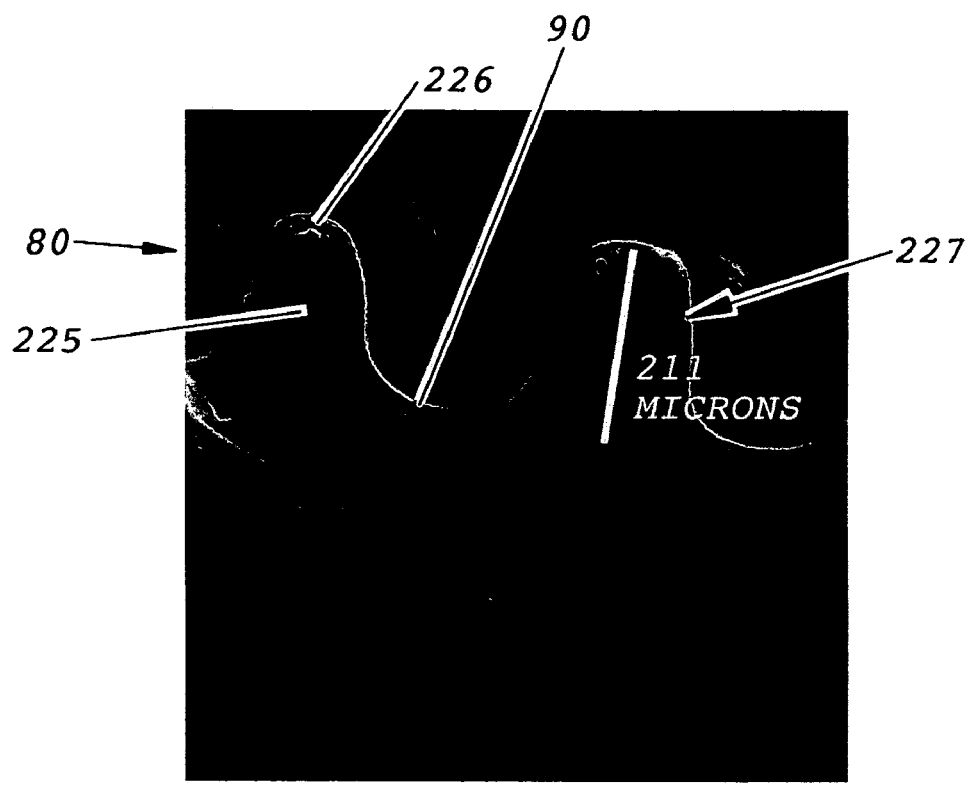
FIG. 19 is a photomicrograph of a portion of a web of the present invention.
Figure 20:
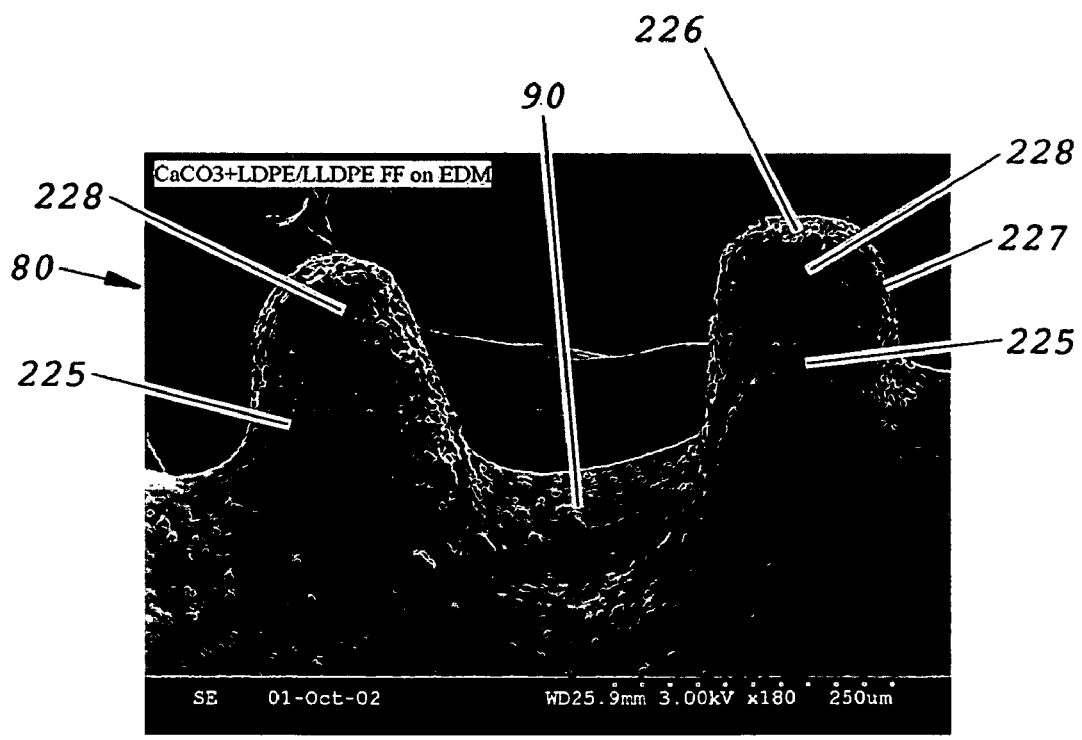
FIG. 20 is an enlarged view of a portion of a web of the present invention.

FIGS. 19 and 20 show greatly enlarged portions of webs 80 made in batch processes on the forming structure shown in FIGS. 13 and 14 to more closely show details of hair-like fibrils 225. The polymer webs 80 shown in FIGS. 19 and 20 have primary apertures 71 (not shown) generally in a penta-hexagon shape, each having a projected area in the first surface 90 of about 1.4 square millimeters. The spacing between primary apertures 71 is such that the open area primary apertures 71 as projected in the first surface 90 is up to 65% of total surface area. The web 80 exhibits about 4,650 hair-like fibrils 225 per square centimeter of first surface 90 area (about 30,000 hair-like fibrils 225 per square inch). This concentration of hair-like fibrils 225 is referred to as the "density" or "area density" of hair-like fibrils 225, and represents the number of hair-like fibrils per unit area of first surface 90, as opposed to total area of polymer web 80. Thus, the regions of polymer web 80 corresponding to primary apertures 71 do not contribute to the area when calculating density. In general, the density is determined by the average center-to-center spacing of the protrusions 2250 on forming structure 350, which is about 150 microns (0.006 inch) for the forming structure shown in FIGS. 13 and 14.

It is believed that a polymer web 80 of the present invention suitable for use as a topsheet on a disposable absorbent article (e.g., a sanitary napkin) should have a density of hair-like fibrils 225 of at least about 1550 per square centimeter (about 10,000 per square inch). The density of hair-like fibrils 225 can be about 2325 per square centimeter (about 15,000 per square inch), and can be about 3100 per square centimeter (about 20,000 per square inch) and can be about 3875 per square centimeter (about 25,000 per square inch). Since for some webs it may be difficult to determine exactly where first surface 90 begins and ends, density can be approximated by taking total area of a predetermined portion of polymer web 80 and subtracting out the area of primary apertures 71 as projected in the first surface 90 of that predetermined portion. The area of primary apertures 71 can be based on the projected area of the depressions 710 of forming structure 350. By "projected area" is meant the area of a surface if it were projected onto a plane parallel to that surface, and can be imagined by analogy, for example, as an "ink stamp" of the surface.

FIG. 19 is a photomicrograph of a web 80 made from a 25 micron (0.001 inch) Dowlex 2045A precursor film 120. As shown, the web 80 of FIG. 19 comprises discrete hair-like fibrils 225, each of the hair-like fibrils 225 being a protruded extension of first surface 90. Each of the hair-like fibrils 225 has a side wall 227 defining an open portion 229 (as shown in FIG. 5) and a closed distal portion 226. The hair-like fibrils 225 shown have a height of about 211 microns, and a diameter at ½ their height of about 142 microns, resulting in an aspect ratio of about 1.5.

The web 80 of FIG. 20 comprises discrete hair-like fibrils 225, each of the hair-like fibrils 225 being a protruded extension of first surface 90. Each of the hair-like fibrils 225 has a side wall 227 defining an open portion 229 (as shown in FIG. 5) and a closed distal portion 226. The hair-like fibrils 225 shown in FIG. 20 have an aspect ratio AR of at least 1.

The difference between the webs 80 shown in FIGS. 19 and 20 is that the precursor film 120 used to make the polymeric web 80 shown in FIG. 20 was a coextruded four layer polyethylene film comprising calcium carbonate in one of the outermost layers. Specifically, the calcium carbonate was added into the polymer melt for the polymer that forms the first surface of web 80 after formation of hair-like fibrils 225. The four layers comprised polyethylene in the follow order: (1) ExxonMobil NTX-137 at about 42 volume percent; (2) ExxonMobil Exact 4151 at about 16 volume percent; (3) ExxonMobil Exact 4049 at about 32 volume percent; and (4) a mixture of 57 weight percent Ampacet 10847 with calcium carbonate blended in as a master batch and 43 weight percent ExxonMobil LD 129, this mixture at a volume percent of about 10 percent. The precursor film 120 had a starting thickness of about 25 microns (0.001 inch).

One interesting and unexpected result of using a $CaCO_3$/PE blend for a skin layer of precursor film 120 is the formation of regions of roughened outer surfaces 228 at or near the distal end 226 of hair-like fibrils 225 as can be seen on the web shown in FIG. 20. These regions of relatively greater surface roughness 228, which have less surface smoothness than the surrounding surfaces, such as first surface 90, provide for a more cloth-like appearance due to its inherent low gloss, and an even greater soft and silky tactile impression. Without being bound by theory, it is believed that the relatively roughened surface texture of the distal ends of hair-like fibrils 225 gives greater texture that is experienced as softness to the skin of a person touching the surface. Without being bound by theory, it is believed that the formation of roughened outer surfaces at or near the distal end 226 of hair-like fibrils 225 is a result of deep drawing precursor web having therein particulate matter. It appears that possibly the particulate matter, in this case $CaCO_3$, causes stress concentrations in the film blend that give rise to surface discontinuities. At the points of maximum strain, i.e., at the point of maximum draw of hair-like fibrils 225, the surface of the film (i.e., precursor film 120) breaks up, exposing particulate matter on the surface of the hair-like fibrils 225.

Therefore, in one embodiment polymer web 80 can be described as having hair-like fibrils 225 in which at least a portion near the distal end 226 thereof exhibits regions of relatively greater surface roughness 228 than the remaining portions. By using different additive particulate matter, the regions of relatively greater surface roughness 228 can provide for other benefits. For example, particulate skin treatments or protectants or odor-absorbing actives can be used. Importantly, webs 80 comprising particulate matter permit actives to be delivered to the skin of a wearer of an article using web 80 in a very direct and efficient manner.

In general, it is believed that any non-diffusing ingredient (particulate and non-particulate) blended into the melt of a polymer of precursor web 120 can be exposed upon strain of the polymer near the distal end of hair-like fibrils 225. Specifically, actives such as skin care agents can be localized substantially at or near distal ends 226 which can be the primary skin contact surfaces for web 80. Other known methods of imparting localized strain to polymeric films can also serve to expose non-diffusing ingredients in layers. For example, embossing, ring rolling, thermovacuum forming, and other known processes can provide for localized rupture and exposure of active ingredients of polymer films.

Other methods of making forming structure 350 include building up the structure by way of localized electroplating, 3-D deposition processes, or photoresist techniques. Photoresist techniques include forming a three dimensional structure by use of an appropriate mask over a liquid photosensitive resin, such as the UV-curable polymer disclosed above. UV curing is effective at curing only the portions of a liquid resin exposed to UV light from a UV light source. The remaining (uncured) portions of the liquid resin can then be washed off, leaving behind only the cured portions. The liquid resin UV-curable polymer can be placed on a tray, for example, to a desired depth or thickness and appropriately masked and UV light-cured to selectively cure the portions to be protrusions 2250 and to not cure the portions that will be the apertures 710. Curing can be done in stages, so that first a negative mask having UV blocking portions corresponding to forming structure apertures 710 (having UV blocking portions in a pattern of teardrops, for example), can be used to first partially cure the polymer by directing a UV light source orthogonal to the mask for a sufficient amount of time. Once the polymer is partially cured in the unmasked areas, a second mask comprising a plurality of closely spaced UV-transparent spots or dots can be placed between the light source and the partially cured polymer. The polymer is again cured by UV-light to fully cure the portions of the polymer that will be the protrusions 2250. Once the protrusions are fully cured, the remaining uncured polymer (and partially cured polymer) can be removed to leave a forming structure having similar characteristics as those shown in FIGS. 15 and 17.

Other methods of making forming structures are contemplated, including creation via a molding technique, in which the forming structure 350 is cast in a negative impression mold, cured, and removed. Also, forming structures could be formed by way of electroplating techniques, in which successive layers of material are built up into a suitable form.

Figure 21:
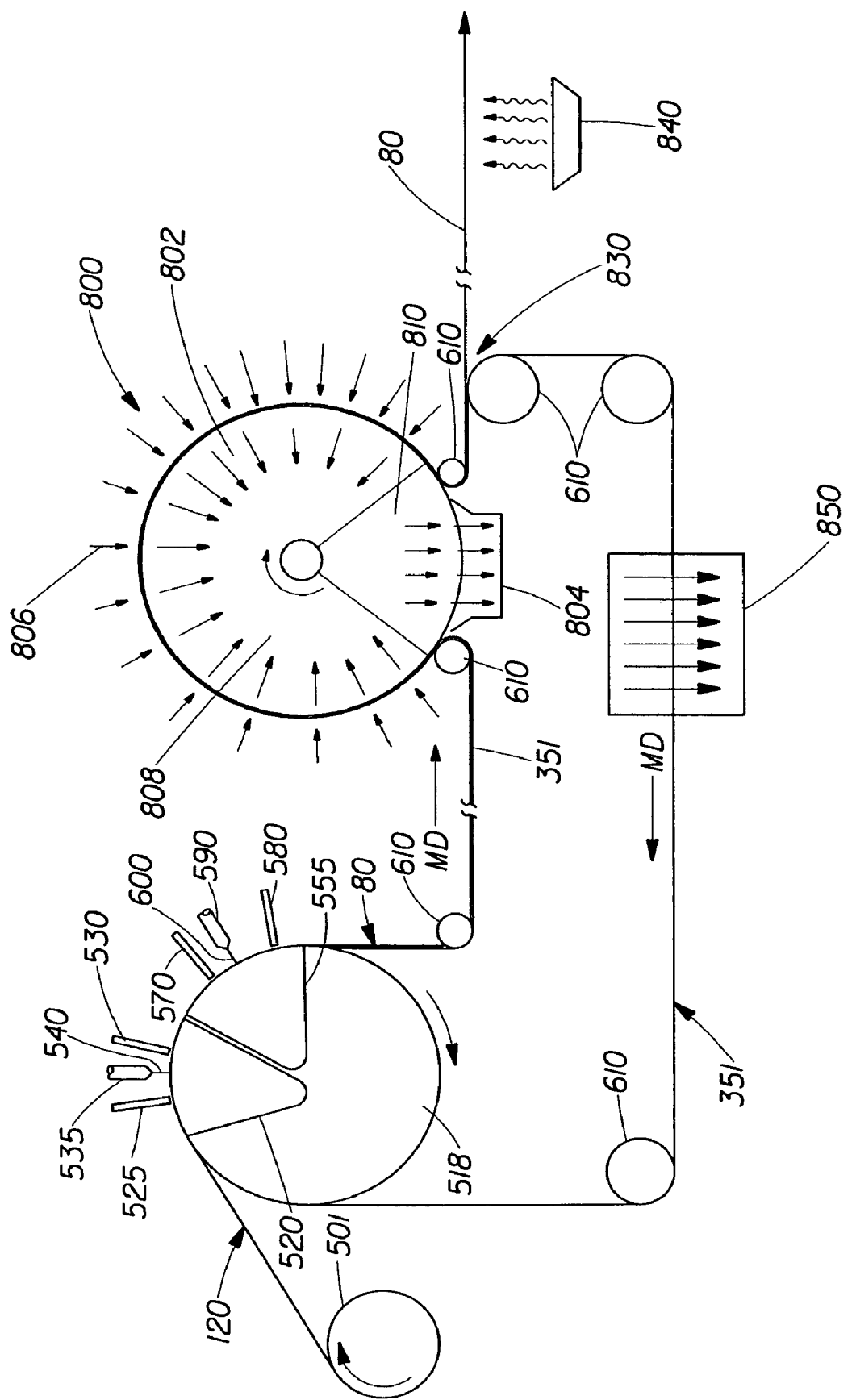
FIG. 21 is a simplified schematic illustration of a process for making a web of the present invention.

One of the advantages to making forming structure 350 from a flexible polymeric material, such as the material described with respect to FIG. 15 is that the forming structure is flexible enough to be utilized as a continuous belt, much like a papermaking belt is used in the above-mentioned Trokhan '289 patent. Such a continuous belt is referred to herein as a flexible "belted" forming structure. By "belted" is meant that the forming structure is in the form of a continuous, flexible band of material, much like a conveyor belt, as opposed to a relatively rigid tubular drum-shaped structure. FIG. 21 shows in simplified schematic representation one embodiment of a process for making a polymeric web 80 of the invention using a flexible belted forming structure 351. As shown, belted forming structure 351 can be a continuous belted member guided and held tensioned by various rollers, e.g., rollers 610. Belted forming structure 351 is guided over forming drum 518. While on forming drum 518 belted forming structure is supported by forming drum 518 and precursor film 120 is supported on forming structure 351. The formation of web 80 on forming structure 351 proceeds the same way as described above with respect to FIG. 9 and forming drum 350. Therefore, precursor web 120 can be subjected to liquid jet 540, (or jets) as well as drying means 590 (or drying/annealing means). However, in the process described schematically in FIG. 21, drying means 590 on forming drum 518 is optional, because drying (and/or annealing) is provided for elsewhere in the process, as described more fully below.

As can be seen in FIG. 21, belted forming structure 351 does not simply rotate on forming drum 518 but is guided onto and off of forming drum 518. As belted forming structure 351 is guided onto forming drum 518 it is dry. After belted forming structure 351 is supported by forming drum 518, or concurrently therewith, precursor web 120 is guided over belted forming structure 351 and hydroformed as described above. After passing drying means 590 the belted forming structure 351 and a three-dimensional, apertured, formed film web 80 of the present invention are guided off of forming drum 518 together. That is, polymer web 80 is intimately in contact with and supported by belted forming structure 351. This permits further processing, such as drying or annealing, if necessary, to take place while the polymer web 80 is still supported by the belted forming structure 351. In this manner, polymer web 80 can endure much greater work without collapsing, tearing, or otherwise deforming in a negative manner.

Belted forming structure 351 and polymer web 80 are guided in the direction indicated in FIG. 21, i.e., the machine direction, to a through-air drying means 800. Through air drying means can be in the form of a rotating drum as shown in FIG. 21, but can be in any of other known configurations. Drying means 800 preferably utilizes air which is forced through polymer web 80 and belted forming structure 351 to effect drying of the web. However, other drying means are contemplated, such as the use of capillary drying or limited orifice drying techniques common in the papermaking industry for drying paper webs.

Drying means shown in FIG. 21 comprises rotating porous drying drum 802. As belted forming structure 351 and polymeric web 80 are supported by drying drum 802 a drying fluid, such as air, is forced through belted forming structure 351 and polymeric web 80. Fluid, such as air, can be forced from the outside to the inside of drying drum 802, as shown in FIG. 21, or it can be forced from the inside to the outside. In either configuration, the point is that the fluid effects drying of polymeric web 80 while web 80 remains fully supported on belted forming structure 351. Drying drum dimensions, fluid flow rates, fluid moisture content, drying drum rotation velocity can all be adjusted as necessary to ensure adequate drying of polymeric web 80 prior to being guided off of drying drum 802.

Drying drum 802 can have a vacuum chamber 808 to aid in fluid flow through polymeric web 80 and belted forming structure 351. Additionally, fluid removal means can be utilized to remove liquid removed from polymeric web 80. Fluid removal means can include a simple drain in forming drum 802, but can also include active removal via pumps as is known in the art to recycle water back to the hydroforming apparatus. Drying drum 802 can have a positive pressure chamber 810 which aids in removing excess moisture from the surface of forming drum 802 prior to repeating the process of supporting belted forming structure 351. Liquid removed can be simply captured in container 804 and removed appropriately, such as by draining into a water recycle system.

Once polymeric web 80 and belted forming structure 351 are guided off of drying drum 802, polymeric web 80 is separated from belted forming structure 351 at separation point 830. From this point polymeric web 80 may be, if necessary, subjected to additional drying, such as by radiant heat drying means 840, and likewise, belted forming structure may be subjected to additional drying means, such as forced air drying means 850. In all cases, other drying means as suitable under the processing conditions can be utilized as necessary to ensure that polymeric web 80 is sufficiently dry prior to final processing into roll stock and belted forming structure 351 is sufficiently dry to avoid introducing moisture into the interior of hair like fibrils 225 of polymeric web 80. Sufficiently dry means dry enough such that post-manufacture moisture related problems such as mold or mildew in the polymeric web are minimized or eliminated.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A polymeric web comprising a polymeric film, said web exhibiting a soft and silky tactile impression on at least one side thereof, said polymeric web comprising a precursor web having a first thickness and a pattern of discrete generally columnar protruded extensions, each of said generally columnar protruded extensions being a protruded extension of said precursor web and having a side wall defining an open proximal portion and a closed distal portion, and wherein said precursor web is thinned at or near said closed distal ends of said generally columnar protruded extensions, wherein said generally columnar protruded extensions have a largest lateral cross-sectional dimension at said proximal portion, wherein said generally columnar protruded extensions have an aspect ratio of at least 0.5.

2. The web of claim 1, wherein said lateral cross-sectional dimensions steadily decrease to said distal portion.

3. The web of claim 1, wherein said sidewalls of said generally columnar protruded extensions decrease in thickness with increasing amplitude of said generally columnar protruded extensions.

4. The web of claim 1, wherein said generally columnar protruded extensions have an average center-to-center spacing of from about 100 microns to 250 microns (0.004 inch to 0.010 inch).

5. The web of claim 1, wherein said silky feeling side of said web exhibits at least about 1500 of said generally columnar protruded extensions per square centimeter.

6. The web of claim 1, wherein said precursor web comprises a multilayer web.

7. The web of claim 6, wherein said precursor web comprises particulate matter in at least one layer.

8. The web of claim 1, wherein said generally columnar protruded extensions are substantially cylindrically shaped.

9. The web of claim 1, wherein said generally columnar protruded extensions have a substantially non-uniform lateral cross section.

10. The web of claim 1, wherein said web further comprises a macroscopically expanded, three-dimensional pattern of macroscopic surface aberrations.

11. The web of claim 1, wherein said generally columnar protruded extensions exhibit an average diameter of at least 100 microns (0.004 inch).

12. The web of claim 1, wherein said generally columnar protruded extensions exhibit an average diameter of between 50 microns (0.002 inch) and 130 microns (0.005 inch).

13. A disposable absorbent article comprising a fluid pervious polymeric web comprising a polymeric film, said polymeric web exhibiting a soft and silky tactile impression on at least one side thereof, said polymeric web comprising a precursor web having a first thickness and a pattern of discrete generally columnar protruded extensions, each of said generally columnar protruded extensions being a protruded extension of said precursor web and having a side wall defining an open proximal portion and a closed distal portion, and wherein said precursor web is thinned at or near said closed distal ends of said generally columnar protruded extensions, wherein said generally columnar protruded extensions have a largest lateral cross-sectional dimension at said proximal portion, and wherein said generally columnar protruded extensions have an aspect ratio of from about 0.5 to 3.

14. The disposable absorbent article of claim 13, wherein said polymeric web further comprises a macroscopically expanded, three-dimensional pattern of macroscopic surface aberrations.

15. The disposable absorbent article of claim 14, wherein said macroscopic surface aberrations comprise apertures.

16. The disposable absorbent article of claim 14, wherein said macroscopic surface aberrations are oppositely oriented from said generally columnar protruded extensions.

17. The disposable absorbent article of claim 13, wherein said article comprises a catamenial device.

18. The disposable absorbent article of claim 17, wherein said catamenial device comprises a sanitary napkin.

19. The disposable absorbent article of claim 18, wherein said polymeric web comprises a topsheet of said sanitary napkin.

20. The disposable absorbent article of claim 13, wherein said generally columnar protruded extensions are substantially cylindrically shaped.

21. The disposable absorbent article of claim 13, wherein said generally columnar protruded extensions have a substantially non-uniform lateral cross section.

22. The disposable absorbent article of claim 13, wherein said lateral cross-sectional dimensions steadily decrease to said distal portion.

23. The disposable absorbent article of claim 13, wherein said sidewalls of said generally columnar protruded extensions decrease in thickness with increasing amplitude of said generally columnar protruded extensions.

24. The disposable absorbent article of claim 13, wherein said precursor web comprises a multilayer polymeric film.

25. The disposable absorbent article of claim 24, wherein said precursor web comprises particulate matter in at least one layer.

26. The disposable absorbent article of claim 13, wherein said generally columnar protruded extensions have an average center-to-center spacing of from about 100 microns to 250 microns (0.004 inch to 0.010 inch).

27. The disposable absorbent article of claim 13, wherein said silky feeling side of said web exhibits at least about 1500 of said generally columnar protruded extensions per square centimeter.

28. The disposable absorbent article of claim 13, wherein said generally columnar protruded extensions exhibit an average diameter of at least 100 microns (0.004 inch).

29. The disposable absorbent article of claim 13, wherein said generally columnar protruded extensions exhibit an average diameter of between 50 microns (0.002 inch) and 130 microns (0.005 inch).

30. The disposable absorbent article of claim 13, said disposable absorbent article further comprising an absorbent core.

31. A fluid pervious polymeric web exhibiting a soft and silky tactile impression on at least one side thereof, said polymeric web comprising a polymeric film, said polymeric web comprising a precursor web having a first thickness and a pattern of discrete generally columnar protruded extensions, each of said generally columnar protruded extensions being a protruded extension of said precursor web and having a side wall defining an open proximal portion and a closed distal portion, wherein said generally columnar protruded extensions have an aspect ratio of at least 0.5, and wherein said precursor web is thinned at or near said closed distal ends of said generally columnar protruded extensions, wherein said generally columnar protruded extensions have a largest lateral cross-sectional dimension at said proximal portion.

32. The fluid pervious polymeric web of claim 31, wherein said polymeric web further comprises a macroscopically expanded, three-dimensional pattern of macroscopic surface aberrations.

33. The fluid pervious polymeric web of claim 32, wherein said surface aberrations comprise apertures.

34. The fluid pervious polymeric web of claim 31, wherein said generally columnar protruded extensions are substantially cylindrically shaped.

35. The fluid pervious polymeric web of claim 31, wherein said generally columnar protruded extensions have a substantially non-uniform lateral cross section.

36. The fluid pervious polymeric web of claim 31, wherein said lateral cross-sectional dimensions steadily decrease to said distal portion.

37. The fluid pervious polymeric web of claim 31, wherein said sidewalls of said generally columnar protruded extensions decrease in thickness with increasing amplitude of said generally columnar protruded extensions.

38. The fluid pervious polymeric web of claim 31, wherein said precursor web comprises a multilayer web.

39. The fluid pervious polymeric web of claim 38, wherein said precursor web comprises particulate matter in at least one layer.

40. The fluid pervious polymeric web of claim 31, wherein said generally columnar protruded extensions have an average center-to-center spacing of from about 100 microns to 250 microns (0.004 inch to 0.010 inch).

41. The fluid pervious polymeric web of claim 31, wherein said silky feeling side of said web exhibits at least about 1500 of said generally columnar protruded extensions per square centimeter.

42. The fluid pervious polymeric web of claim 31, wherein said generally columnar protruded extensions exhibit an average diameter of at least 100 microns (0.004 inch).

43. The fluid pervious polymeric web of claim 31, wherein said generally columnar protruded extensions exhibit an average diameter of between 50 microns (0.002 inch) and 130 microns (0.005 inch).

* * * * *